US009823325B2

(12) United States Patent
Bennett

(10) Patent No.: US 9,823,325 B2
(45) Date of Patent: Nov. 21, 2017

(54) METHODS AND COMPOSITIONS RELATING TO REPORTER GELS FOR USE IN MRI TECHNIQUES

(76) Inventor: Kevin M. Bennett, Chandler, AZ (US)

(*) Notice: Subject to any disclaimer, the term of this patent is extended or adjusted under 35 U.S.C. 154(b) by 1214 days.

(21) Appl. No.: 13/515,215

(22) PCT Filed: Dec. 14, 2010

(86) PCT No.: PCT/US2010/060282
§ 371 (c)(1),
(2), (4) Date: Sep. 20, 2012

(87) PCT Pub. No.: WO2011/075476
PCT Pub. Date: Jun. 23, 2011

(65) Prior Publication Data
US 2013/0022548 A1 Jan. 24, 2013

Related U.S. Application Data

(60) Provisional application No. 61/286,084, filed on Dec. 14, 2009.

(51) Int. Cl.
A61K 9/00 (2006.01)
G01R 33/56 (2006.01)
A61K 49/12 (2006.01)
A61K 49/14 (2006.01)
A61K 49/18 (2006.01)
(Continued)

(52) U.S. Cl.
CPC .......... *G01R 33/5601* (2013.01); *A61K 49/12* (2013.01); *A61K 49/14* (2013.01); *A61K 49/1803* (2013.01); *A61K 49/1887* (2013.01); *A61L 15/54* (2013.01); *A61L 15/60* (2013.01); *A61L 27/50* (2013.01); *A61L 27/52* (2013.01); *A61L 29/145* (2013.01); *A61L 29/18* (2013.01); *A61L 31/145* (2013.01); *A61L 31/18* (2013.01); *G01N 24/08* (2013.01)

(58) Field of Classification Search
CPC .................................................. G01R 33/5601
See application file for complete search history.

(56) References Cited

U.S. PATENT DOCUMENTS 4,729,892 A * 3/1988 Beall .................. A61K 49/1803
424/9.3
5,514,379 A * 5/1996 Weissleder ........... A61K 9/1658
424/426
(Continued)

OTHER PUBLICATIONS

Uchida et al, A Human Ferritin Iron Oxide Nano-composite Magnetic Resonance Contrast Agent, 2008, 60, 1073-1081.*
(Continued)

Primary Examiner — Paul Dickinson
(74) Attorney, Agent, or Firm — Booth Udall Fuller, PLC

(57) ABSTRACT

The present invention describes methods and compositions for non-invasively assessing the molecular structure of biocompatible hydrogels using MRI analysis. It is shown that biocompatible hydrogels prepared from polymerizing macromolecules that are attached to a paramagnetic, superparamagnetic or ferromagnetic contrast agents form reporter gels wherein monitoring of the changes in the structure of the hydrogels by MRI is facilitated by the presence of such paramagnetic, superparamagnetic or ferromagnetic agents in the biocompatible hydrogel.

20 Claims, 7 Drawing Sheets

(51) Int. Cl.
- A61L 15/54 (2006.01)
- A61L 15/60 (2006.01)
- A61L 27/50 (2006.01)
- A61L 27/52 (2006.01)
- A61L 29/14 (2006.01)
- A61L 29/18 (2006.01)
- A61L 31/14 (2006.01)
- A61L 31/18 (2006.01)
- G01N 24/08 (2006.01)

(56) References Cited

U.S. PATENT DOCUMENTS

| | | | |
|---|---|---|---|
| 7,407,646 B2 * | 8/2008 | Laurent | C08K 9/08 424/1.29 |
| 2004/0175371 A1 | 9/2004 | Yacoby-Zeevi | |
| 2004/0197369 A1 | 10/2004 | Hubbell et al. | |
| 2006/0293581 A1 | 12/2006 | Plewes et al. | |
| 2007/0036727 A1 | 2/2007 | Aime et al. | |
| 2007/0106208 A1 | 5/2007 | Uber et al. | |
| 2007/0258889 A1 | 11/2007 | Douglas et al. | |
| 2008/0114235 A1 | 5/2008 | Unal et al. | |

OTHER PUBLICATIONS

The International Search Report and Written Opinion as dated Feb. 11, 2011 for International Application No. PCT/US2010/060282.

Kevin M. Bennett, et al., "Controlled Aggregation of Ferritin to Modulate MRI Relaxivity," Biophys J., Jul. 2008, vol. 95, pp. 342-351.

Kevin M. Bennett, et al., "MRI of the Base Membrane Using Charged Nanoparticles as Contrast Agents." Magnetic Resonance in Medicine, Sep. 2008, vol. 60, pp. 564-574.

Min Kyoon Shin, et al., "Controlled Magnetic Nanofiber Hydrogels by Clustering Ferritin," Langmuir, Nov. 2008, vol. 21, pp. 12107-12111.

* cited by examiner

NF  CF  CF+trypsin  CF+trypsin + inhibitor

METHODS AND COMPOSITIONS RELATING TO REPORTER GELS FOR USE IN MRI TECHNIQUES

RELATED APPLICATIONS

This application is a 371 application of PCT/US2010/060282 filed Dec. 14, 2010 which claims priority based on U.S. Patent Application No. 61/286,084 filed Dec. 14, 2009.

FEDERALLY SPONSORED RESEARCH OR DEVELOPMENT

[Not Applicable]

FIELD OF THE INVENTION

The present invention relates to methods and compositions for use of biocompatible hydrogels as magnetic resonance imaging (MRI) reporter gels to report on gel macromolecular structure, enzymes and tissue structure using magnetic resonance imaging.

BACKGROUND OF THE INVENTION

There are numerous applications in which implantable hydrogels or compositions are implanted into mammals for purposes of drug delivery, and tissue regeneration. Hydrogels are generally defined as polymeric materials that swell in water and other fluids, absorbing the fluid within the polymer network without dissolving. Hydrophilic hydrogels have a large amount of water content at equilibrium, and good biocompatibility.

Hydrogel matrices have been developed to promote tissue regeneration after injury, and to locally deliver drugs. In tissue regeneration, the chemical makeup and structural alignment of the gel can influence the way cells attach and move through it, and much work is being done to rationally design gels as synthetic tissue analogues to support cell regrowth after injury [15-19]. For example, synthetic hyaluronic acid gels have been used to guide neurons to the site of a spinal cord injury, with the aim of completely regaining spinal cord function [18, 20]. Many synthetic hydrogels are structurally similar to biological hydrogels, but have a simplified, well-controlled structure. These constructs are important physical models used to understand the structure and function of the extracellular matrix. The gel structures have been sensitized to local enzymatic degradation, temperature, and cell growth [16, 17, 21-25]. This is important in polymer gels with controlled-release properties, which are designed to deliver drugs upon changes in the local microenvironment [26-28].

Upon implantation of the hydrogel device, interaction of these hydrogels with the surrounding tissue is complex, making it important to monitor the molecular structure of the gels once implanted. Molecular imaging methods have been developed to provide real-time, in vivo spatial maps of molecules. Several molecular imaging modalities are now widely used, and show promise for detecting molecules in humans noninvasively in the clinic. Optical imaging, in particular, has been successful in highly sensitive detection of molecules, as demonstrated by the routine use of fluorescent reporter proteins in cellular and animal experiments, and in vivo confocal microscopy is used to study cell and vascular function in humans during surgery [29-31]. However, optical imaging suffers from a limited penetration of light, making imaging at depths of over a few centimeters difficult. Other technologies, such as PET, CT, and SPECT, offer whole-body penetration, but have limited resolution and rely on ionizing radiation for contrast [32]. Radioopaque polymers are used to detect gels with x-ray and CT [1,9], and fluorescent conjugates are commercially available for labeling gel molecules for optical imaging [33, 34]. Nevertheless, while these techniques hold some promise, none allows for a non-invasive techniques allows for non-invasive, three-dimensional imaging of gel structure after implantation in animals and humans. Thus, once the gel is implanted, there is currently no method of determining whether the payload in the gel has been delivered or whether the gel has attracted the appropriate cells for regeneration.

Thus, there remains a need for a hydrogel composition that can report on its physical status within the body in a noninvasive, three dimensional manner.

BRIEF SUMMARY OF THE INVENTION

The present invention in some preferred aspects describes a method of method of non-invasively assessing the molecular structure of biocompatible hydrogel comprising subjecting the biocompatible hydrogel to MRI analysis wherein the biocompatible hydrogel is prepared from polymerizing macromolecules that are attached to a paramagnetic, superparamagnetic or ferromagnetic agent wherein changes in the structure of the hydrogel are monitored by MRI facilitated by the presence of the paramagnetic contrast agent in the biocompatible hydrogel.

Paramagnetic, superparamagnetic or ferromagnetic agents are well known to those of skill in the art and any such agents may be incorporated into hydrogels for use in the methods described herein. In exemplary embodiments, the paramagnetic contrast agent comprises a metal ion selected from the group consisting of suitable Gd(III), Mn(II), Cu(II), Cr(III), Fe(III), Co(II), Er(II), Ni(II), Eu(III) and Dy(III).

In specific preferred embodiments, the paramagnetic contrast agent comprises a superparamagnetic iron oxide (SPIO). Preferably, the paramagnetic contrast agent comprises a SPIO-containing nanoparticle.

In other embodiments, the paramagnetic contrast agent comprises ferritin bound to an iron oxide moiety.

Other aspects of the invention contemplate methods of non-invasively assessing the molecular structure of biocompatible hydrogel comprising subjecting the biocompatible hydrogel to MRI analysis wherein the biocompatible hydrogel is prepared from polymerizing macromolecules that are attached to MRI-detectable superparamagnetic nanoparticle-containing contrast agent wherein the polymerization state of the hydrogel is monitored by MRI facilitated by the aggregation and disaggregation of the nanoparticles present in the biocompatible hydrogel.

In the methods of the invention, the hydrogel may be any biocompatible, biodegradable polymer gel typically used in the art. Exemplary such gels are made from biocompatible, biodegradable polymers selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof.

Other exemplary hydrogels are made of a polymeric material that comprises one or more recurring units selected from linear (siloxanyl)alkyl (meth)acrylates, branched (siloxanyl)alkyl (meth)acrylates, cyclic (siloxanyl)alkyl (meth)acrylates, silicone-containing (meth)acrylates, fluorine-containing (meth)acrylates, hydroxyl group containing (meth)acrylates, (meth)acrylic acid, N-(meth)acryloylpyrrolidone, (meth)acrylamides, aminoalkyl (meth)acrylates, alkoxy group-containing (meth)acrylates, aromatic group containing (meth)acrylates, glycidyl (meth)acrylate, tetrahydrofurfuryl (meth)acrylate, silicone-containing styrene derivatives, fluorine-containing styrene derivatives, styrene derivatives, and vinyl monomers.

In specific embodiments, the hydrogel is an artificial extracellular matrix gel. In particular preferred embodiments, the extracellular matrix gel is collagen or Matrigel®.

In exemplary methods, the MRI imaging is conducted after the hydrogel has been implanted into an in vivo site in a mammal.

Other specific embodiments contemplate methods in which the hydrogel further comprises a zymogen wherein the zymogen is activated in vivo initiate degradation of the gel.

In certain embodiments, the hydrogel comprises between 50 nM to 20 mM paramagnetic contrast agent. In other embodiments, the hydrogel comprises between 1 µM and 1 mM zymogen. The zymogen are embedded in reporter gels to make the degradation rates of the gels highly sensitive to target molecules for the zymogens. Any zymogen may be used to amplify the degradation rates of the gels. Exemplary zymogens that can be incorporated into the gels include but are not limited to a zymogen is selected from the group consisting of a trypsinogen, a heparinase, a hyaluronidase, a chymotrypsinogen, a pepsinogen, a caspase, a proelastase, and a prolipase.

Other methods of the invention relate to methods of selectively detecting the controlled release at a target site of a substance contained in a hydrogel of the invention, comprising implanting the hydrogel at the target site; contacting the hydrogel with an enzyme to activate the zymogen; and monitoring the changes in the hydrogel structure using MRI imaging to determine the rate of controlled release of the substance from the hydrogel.

In specific embodiments, the hydrogel is implanted in vivo and the aggregation and disaggregation of the nanoparticles in the biocompatible hydrogel results from the interaction of the hydrogel with cells of the extracellular matrix. More particularly, the interaction of the hydrogel with cells of the extracellular matrix comprises invasion of the hydrogel by cells of the extracellular matrix.

In other embodiments, the hydrogel is implanted in vivo and the aggregation and diaggregation of the nanoparticles in the biocompatible hydrogel results from the interaction of the hydrogel degradative enzymes from the site of implantation that cause a disintegration of the hydrogel. In specific aspects, the presence of the zymogen increases the rate of release of the substance as compared to the release of such substance from a gel that does not comprise the zymogen.

Also contemplated herein are methods of selectively detecting the release at a target site of a substance contained in a hydrogel of the invention, comprising implanting the hydrogel at the target site, and monitoring the changes in the hydrogel structure using MRI imaging to determine the rate of controlled release of the substance from the hydrogel.

The invention further comprises in vitro methods of non-invasively detecting the migration of cells into an implanted extracellular matrix site in vivo comprising applying MRI analysis to the area of the implanted extracellular matrix; determining the integrity of the implanted extracellular matrix, wherein the extracellular matrix comprises a biocompatible hydrogel prepared from polymerizing macromolecules that are attached to a paramagnetic contrast agent; wherein migration of cells into the implanted extracellular matrix is seen as a change in the MRI image of the implanted extracellular matrix.

In specific such embodiments, the hydrogel may further comprises a growth factor to facilitate recruitment of cells to the site of the implanted extracellular matrix. In addition to, or instead of a growth factor, the hydrogels also may comprise a drug or other therapeutic agent to be delivered at the site of implantation or at a site distal to the site of implantation.

BRIEF DESCRIPTION OF SEVERAL VIEWS OF THE DRAWINGS

The following drawings form part of the present specification and are included to further illustrate aspects of the present invention. The invention may be better understood by reference to the drawings in combination with the detailed description of the specific embodiments presented herein.

DETAILED DESCRIPTION OF THE INVENTION

Figure 1A:
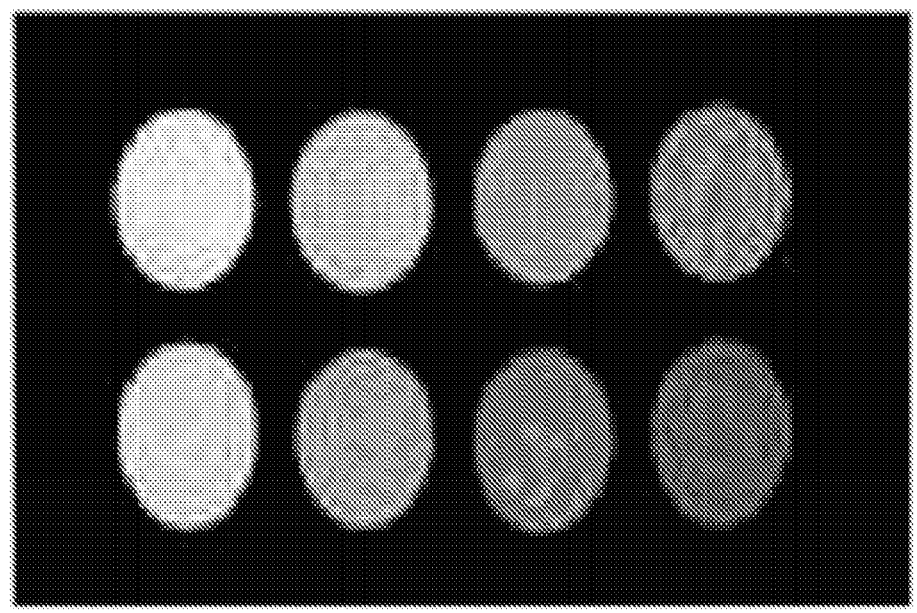
FIG. 1: (a) Short-length cross-linking of cationized ferritin reduces MRI signal compared to uncrosslinked controls. The images were taken with a CPMG pulse sequence with TE/TR=6/3000 ms. The samples were embedded 1:1 in 2% agarose. (b) Effects of cross-linker (DTSSP) concentration on apparent R2 of ferritin aggregates. The increase in R2 with ferritin aggregation was reversed by cleaving the cross-linker with DTT.

The present invention addresses the need for a self-reporting hydrogel composition by providing biocompatible hydrogels that report on gel macromolecular structure and enzyme activity using MRI. Biocompatible hydrogels are known to those skilled in that art that have been developed as synthetic tissues to guide cell growth, deliver drugs, and support tissue regeneration in humans. A major limitation of those implantable hydrogel-based synthetic tissues is that their molecular structures cannot be assessed noninvasively. Cell growth and the specificity of targeted drugs in the gels must therefore be assessed by biopsy, which is invasive and disrupts the macromolecular structure of the gel.

In the present invention, the deficiencies in the prior art gels are overcome by basic reporter gel constructs, containing functionalized MRI-contrast agent containing nanoparticles, to report on cells and enzymes that alter the molecular structure of the implanted devices in vitro and in vivo. In specific embodiments, these biologically-based MRI reporter gels contain functionalized superparamagnetic nanoparticles that can be used in MRI imaging techniques to yield highly sensitive detection of cells and enzymes that invade or come into contact with the hydrogels. The MRI relaxivity of superparamagnetic nanoparticles is modulated through controlled aggregation. When the nanoparticles are attached to a polymerizing macromolecule, the aggregation and disaggregation of the nanoparticles can be used to detect the polymerization state of the macromolecule with MRI. This property is exploited herein to prepare hydrogels that are doped with MRI-detectable super-paramagnetic nanoparticle contrast agents that bind to macromolecules within the gel. The MRI relaxation times will then be used to determine the structure of these macromolecules.

In addition to containing super-paramagnetic nanoparticle contrast agents, the reporter hydrogels also will contain zymogens as sites for digestion by proteolytic and glycolytic enzymes. In this manner, the hydrogels can be monitored to detect the presence of cells and enzymes in a noninvasive manner using MRI imaging techniques known to those of skill in the art.

The synthetic reporter gels described herein can be implanted in vivo, to promote wound healing and study cell-ECM interactions in animal models and humans, as scaffolds for drug delivery and the like. By implanting these in vivo and monitoring the integrity of the gels using MRI techniques, it is possible to detect the presence of the cells and specific molecules near and or affecting the gels using MRI.

MRI is an important diagnostic tool for producing a noninvasive, non-radioisotope-based assessment of biological tissue. (Bulte et al. "Magnetic resonance microscopy and histology of the CNS," Trends in Biotechnology, 2002, 20, S24-S28). Advantages of MRI as an imaging modality as compared to other imaging techniques include its lack of ionizing radiation, high spatial resolution, and flexibility in contrast. MRI offers the advantage of whole-tissue penetration with high resolution (hundreds of microns in each dimension) in a reasonable period of time. MRI has also been used to obtain information about molecular events in vivo [35-39]. Several groups have reported endogenous MRI properties of synthetic and biologically derived hydrogels [24, 40-45]. These studies have relied on changes in transverse and longitudinal (T2 and T1) relaxation rates in the gels to determine bulk gel structure, but have not studied specific changes in the gel macromolecules. The MRI reporter gels of the present invention allow for the detection of the development and rearrangement of the extracellular matrix (ECM) in animals and humans. Additionally, the gels can be used as scaffolds to test the action of various agents, and are invaluable as well-controlled models of the extracellular matrix (ECM).

The hydrogels are prepared by linking to the polymer of the hydrogel a superparamagnetic contrast agent such as for example, superparamagnetic iron oxide nanoparticles (SPIOs). SPOIs have been used as MRI contrast agents in a broad range of biological applications [46-49] and create a create a static magnetic field perturbation in the presence of an applied magnetic field. This perturbation causes a change in the local water proton precession (Larmour) frequency in MRI. If a gradient-echo (T2*-weighted) pulse sequence is used, the static field perturbation causes an increase in phase dispersion in the sample, and decreases the MRI signal. The size of the perturbation, and the magnitude of the signal decrease, are determined by how the SPIOs are clustered. In gradient echo MRI using targeted SPIOs as contrast agents, the particles show up as dark pixels in the image relative to background. If a spin-echo (T2-weighted) pulse sequence is used, this static dephasing is refocused. In this case, only spins moving through the perturbation during the experiment are dephased. In general, spin-echo techniques are therefore less sensitive to the static field offset caused by the presence of SPIOs, but they have the advantage of being more sensitive to the sub-pixel aggregation of these particles [46, 50-54]. This effect has recently been demonstrated using ferritin, an iron storage protein used as an SPIO contrast agent [53]. The aggregation of ferritin was shown to modulate the T2 relaxivity (R2) in an agarose gel by inter-ferritin crosslinking. Actin-bound ferritin was also used to modulate the MRI signal by actin polymerization. An important feature of SPIO aggregation is that both T2- and T2*-weighted images, probed by spin-echo and gradient-echo pulse sequences, respectively, are modulated by aggregation.

Examples of paramagnetic metals include the elements having atomic numbers of 22 to 29, 42, 44 and 58-70. Examples of such metals are chromium (III), manganese (II), iron (II), iron (III), cobalt (II), nickel (II), copper (II), praseodymium (III), neodymium (III), samarium (III), gadolinium (III), terbium, (III), dysprosium (III), holmium (III), erbium (III) and ytterbium (III). Chromium (III), manganese (II), iron (III) and gadolinium (III) are preferred. In the present invention, these metal ions are chelated or otherwise linked hydrogel-forming macromolecules and the hydrogels are then prepared from the macromolecules using conventional methods.

The hydrogel compositions may be any type of hydrogel typically used as a biocompatible implantable composition. For example, the hydrogel may be a polyvinyl alcohol hydrogels (PVA-H) prepared by physically crosslinking an aqueous solution of polyvinyl alcohol (PVA) to produce a gel. The crosslinking is accomplished by subjecting the aqueous PVA solution to multiple cycles of freezing and thawing. Such hydrogels are described in U.S. Pat. No. 5,981,826 and U.S. Pat. No. 6,268,405.

In other examples, the hydrogel, may be an agarose hydrogel or other hydrogel known in the art. In other embodiments, the spacer material may be another gel or gel-like material, such as polyethylene glycol, agarose, alginate, polyvinyl alcohol, collagen, Matrigel®, chitosan, gelatin, or combination thereof.

The gel matrix is selected to have properties that allow the therapeutic agent to be expressed within the gel matrix, as well as allowing the expressed therapeutic agent to diffuse out of the gel matrix into the surrounding environment.

Examples of gel matrices that may be used include, but are not limited to, collagen gel, fibrin glue, polyglycolic acid, polylactic acid, polyethylene oxide gel, alginate or calcium alginate gel, poly-(2-hydroxyethyl methacrylate) (i.e., a hydrogel), polyorthoester, hyaluronic acid, polyanhydride, chitosan, gelatin, agarose, and other bioresorbable and biocompatible materials such as those described in EP 0705878 A2. In other embodiments, the hydrogel comprises agar, agarose, gellan gum, arabic gum, xanthan gum, carageenan, alginate salts, bentonite, ficoll, pluronic polyols, CARBOPOL, polyvinylpyrollidone, polyvinyl alcohol, polyethylene glycol, methyl cellulose, hydroxymethyl cellulose, hydroxyethyl cellulose, carboxymethyl cellulose, carboxymethyl chitosan, poly-2-hydroxyethyl-meth-acrylate, polylactic acid, polyglycolic acid, collagen, gelatin, a plastic, or a combination of any thereof. Poly 2-hydroxyethyl methacrylate (pHEMA) hydrogels are known to those skilled in the art and have been used as biocompatible gels.

Polysaccharides are a class of macromolecules of the general formula $(CH_2O)n$ which are also useful as the hydrogel substrate in the present invention. Polysaccharides include several naturally occurring compounds, e.g., agarose, alginate and chitosan. Agarose is a clear, thermoreversible hydrogel made of polysaccharides, mainly the alternating copolymers of 1,4 linked and 3,6-anhydro-.alpha.-L-galactose and 1,3 linked .beta.-D-galactose. Two commercially available agaroses are SeaPrep™ and SeaPlaque™ agarose (FMC Corp. Rockland, Me.). The thermoreversible properties of agarose gels make it possible for agarose to be a liquid at room temperature allowing for easy mixing of cell-gel solution and then cooling to 4° C. causes gelation and entrapment of cells. This is a comparatively benign process, free of chemicals toxic to the cells.

The agarose concentration can be about 0.50 to 2% (w/v), most preferably about 1.0%. Alginate is a carbohydrate polymer isolated from seaweed, which can be crosslinked to form a hydrogel by exposure to a divalent cation such as calcium, as described, for example in WO 94/25080, the disclosure of which is incorporated herein by reference. The modified alginate solution is mixed with the superparamagnetic contrast agent to form a suspension. Then the polymer in the suspension is crosslinked to form the hydrogel containing the superparamagnetic contrast agent. The crosslinking is achieved to form a hydrogel in the presence of physiological concentrations of calcium ions (See e.g., U.S. Pat. No. 4,352,883 to Lim, incorporated herein by reference).

In general, the polymers that make up the biological gels are at least partially soluble in aqueous solutions, such as water, buffered salt solutions, or aqueous alcohol solutions. Methods for the synthesis of the polymers are known to those skilled in the art (See e.g., Concise Encyclopedia of Polymer Science and Polymeric Amines and Ammonium Salts, E. Goethals, editor (Pergamen Press, Elmsford, N.Y. 1980)). Naturally occurring and synthetic polymers may be modified using chemical reactions available in the art and described, for example, in March, "Advanced Organic Chemistry," 4th Edition, 1992, Wiley-Interscience Publication, New York.

In specific embodiments, the hydrogel matrix can be a biological or synthetic hydrogel, including alginate, crosslinked alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly(ethylene oxide)-poly(propylene oxide), poly(vinyl alcohol), polyacrylate, platelet rich plasma (PRP) clot, platelet poor plasma (PPP) clot, Matrigel, or blends thereof.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Several physical properties of the biological gels are dependent upon gel concentration. Increase in gel concentration may change the gel pore radius, morphology, or its permeability to different molecular weight proteins. Gel pore radius determination can be effected by any suitable method, including hydraulic permeability determination using a graduated water column, transmission electron microscopy and sieving spheres of known radius through different agar gel concentrations (See, e.g., Griess et al., (1993) Biophysical J., 65:138-48).

A variety of other suitable biological gels are also known. The polymer can be mixed with the superparamagnetic contrast agent and the polymer can then be crosslinked to form a hydrogel matrix containing the superparamagnetic contrast agent prior to implantation of the gel into the body. A hydrogel is defined as a substance formed when an organic polymer (natural or synthetic) is crosslinked via covalent, ionic, or hydrogen bonds to create a three-dimensional open-lattice structure which entraps water molecules to form a gel.

One skilled in the art will appreciate that the volume or dimensions (length, width, and thickness) of the biological gel comprising the contrast agent can be selected based on the region or environment into which the biological gel substrate is to be implanted. In one embodiment, the biological gel has a length (defined by a first and second long end) of about 10 cm to about 30 cm. The biological gel can further have a length of about 15 cm to about 25 cm. In a preferred embodiment, the biological gel has a length of about 20 cm. In another embodiment, the biological gel has a width (defined by a first and second short end) of about 0.5 cm to about 4.0 cm. The biological gel can further have a width of about 1.0 cm to about 3.0 cm. In a preferred embodiment, the biological gel has a biocompatible substrate with width of about 2.0 cm.

In certain embodiments, the MRI-contrast agent containing reporter gels of the invention also may comprise a therapeutic agent. Such a therapeutic agent may advantageously be delivered to tissues adjacent or tissues proximal to the site of implantation of the hydrogels of the invention. The delivery and effects of the therapeutic agent can then be monitored using standard MRI techniques. Biologically-active agents which may be used added to the hydrogels and implanted to a site in vivo include, for example, a medicament, drug, or other suitable biologically-, physiologically-, or pharmaceutically-active substance which is capable of providing local or systemic biological, physiological, or therapeutic effect in the body of the patient. The biologically-active agent is capable of being released from the hydrogel implant and the presence of the superparamagnetic component in the hydrogels allows a real-time monitoring of the hydrogel implant and its adjacent or surrounding tissue during biodegradation, bioerosion, or bioresorption of the hydrogel implant.

Other agents may be included in the reporter hydrogels described herein preferably are capable of preventing infection in the host, either systemically or locally at the implantation site. These additives include anti-inflammatory agents, such as hydrocortisone, prednisone, and the like, NSAIDS, such as acetaminophen, salicylic acid, ibuprofen, and the like, selective COX-2 enzyme inhibitors, antibacterial agents, such as penicillin, erythromycin, polymyxin B, viomycin, chloromycetin, streptomycins, cefazolin, ampicillin, azactam, tobramycin, cephalosporins, bacitracin, tetracycline, doxycycline, gentamycin, quinolines, neomycin, clindamycin, kanamycin, metronidazole, and the like, antiparasitic agents such as quinacrine, chloroquine, vidarabine, and the like, antifungal agents such as nystatin, and the like, antiviricides, particularly those effective against HIV and hepatitis, and antiviral agents such as acyclovir, ribarivin, interferons, and the like. Systemic analgesic agents such as salicylic acid, acetaminophen, ibuprofen, naproxen, piroxicam, flurbiprofen, morphine, and the like, and local anaesthetics such as cocaine, lidocaine, bupivacaine, xylocalne, benzocaine, and the like, also can be used as drugs to be delivered by the hydrogels.

Examples of biologically active agents that are useful include substances capable of preventing an infection systemically in an animal or locally at the defect site, for example, anti-inflammatory agents such as hydrocortisone or prednisone; antibacterial agents such as penicillin, cephalosporins, bacitracin, tetracycline, doxycycline, gentamycin, quinolines, neomycin, clindamycin, kanamycin, or metronidazole; antiparasitic agents such as quinacrine, chloroquine, or vidarabine; antifungal agents such as nystatin; antiviral agents such as acyclovir, ribarivin, or interferons; analgesic agents such as acetaminophen, ibuprofen, naproxen, piroxicam, flurbiprofen, or morphine; local anesthetics such as cocaine, lidocaine, bupivacaine, and benzocaine.

Other therapeutic agents include bioactive agents such as those selected from the group consisting of: an antisense nucleotide, a thrombin inhibitor, an antithrombogenic agent, a tissue plasminogen activator, a thrombolytic agent, a fibrinolytic agent, a vasospasm inhibitor, a calcium channel blocker, a nitrate, a nitric oxide promoter, a vasodilator, an antimicrobial agent, an antibiotic, an antiplatelet agent, an antimitotic, a microtubule inhibitor, an actin inhibitor, a remodeling inhibitor, an agent for molecular genetic intervention, a cell cycle inhibitor, an inhibitor of the surface glycoprotein receptor, an antimetabolite, an antiproliferative agent, an anti-cancer chemotherapeutic agent, an anti-inflammatory steroid, an immunosuppressive agent, an antibiotic, a radiotherapeutic agent, iodine-containing compounds, barium-containing compounds, a heavy metal functioning as a radiopaque agent, a peptide, a protein, an enzyme, an extracellular matrix component, a cellular component, a biologic agent, an angiotensin converting enzyme (ACE) inhibitor, ascorbic acid, a free radical scavenger, an iron chelator, an antioxidant, a radiolabelled form or other radiolabelled form of any of the foregoing, or a mixture of any of these.

In some preferred embodiments, the hydrogels may comprise agents that facilitate the recruitment of cells to the site of the hydrogel implant. For example, the hydrogels may comprise a neurotrophic factor (BDNF) or hyaluronic acid, will be added to the gel to promote neurite and astrocytic growth. Other growth factors that may be includes either alone or in combination include but are not limited to epidermal growth factor; leukocyte adhesion molecules; neurotrophins (including brain-derived neurotrophic factor (BDNF), nerve growth factor, and neurotrophin 3; osteogenic growth peptide, platelet-derived growth factor (PDGF); fibroblast growth factor (FGF); erythropoietin; stem cell factor; insulin-like growth factor; colony stimulating factors (e.g., granulocyte-macrophage colony-stimulating factor, granulocyte colony-stimulating factor, and macrophage colony-stimulating factor and analogs); lymphocyte activating peptide; tuftsin; prolactin; angiotensin, transforming growth factor (TGF); Bone morphogenetic proteins (BMPs); and dynorphin and analogs thereof.

Substances which are capable of promoting growth and survival of cells and tissues or augmenting the functioning of cells, or metabolic precursors thereof are also useful biologically active agents, for example, a nerve growth promoting substance such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGP), insulin-derived growth factor (IGF-I, IGF-II), transforming growth factor alpha (TGF-I), transforming growth factor beta (TGF-I), epidermal growth factor (EGF), fibroblast growth factor (FGF), or interleukin-1 (IL-1); an osteoinductive agent or bone growth promoting substance such as bone chips, or demineralized freeze-dried bone material; antineoplastic agents such as methotrexate, 5-fluorouracil, floxuridine, adriamycin, vinblastine, cisplatin, tumor-specific antibodies conjugated to toxins or tumor necrosis factor (TNF).

Other useful substances include hormones such as progesterone, testosterone, and follicle stimulating hormone (FSH) (birth control, fertility enhancement), insulin, or somatotrophins; calcitonin; pituitary adenylate cyclase activating polypeptide; cholecystokinin; pepstatin; bestatin, antihistamines such as diphenhydramine, or chlorpheniramine; cardiovascular agents such as digitalis, nitroglycerine, papaverine, or streptokinase; anti-ulcer agents such as cimetidine hydrochloride, or isopropamide iodide; bronchodilators such as metaproternal sulfate, or aminophylline; vasodilators such as theophylline, niacin or minoxidil; central nervous system agents such as a tranquilizer, 1-adrenergic blocking agents, or dopamine; antipsychotic agents such as risperidone, olanzapine; narcotic antagonists such as naltrexone, naloxone or buprenorphine. Luteinizing hormone and releasing hormone; Neurotensin; Bombesin; Glucagon-like peptide; Pancreastatin; chromogranins A, B and C; Endorphins; Protein kinase C; Amyloid, amyloid fibrin, fragments and analogues; Calpain and other calmodulin-inhibitory proteins; Charybdotoxin, Apamin and analogs; Phospholipase A2 and receptor inhibiting/activating peptides and analogs.

Another class of bioactive agents having a nucleophilic group is the nucleotides, oligonucleotides, polynucleotides and corresponding nucleosides and nucleic acids. These molecules have such bioactive functions as antiviral agents, antibacterial agents, anticancer agents, antisense agents, per probes and the like. Examples include AZT, aminouracil, carbovir, acyclovir, valacyclovir methotrexate, purine and pyrimidine nucleosides such as L-deoxynucleosides (the native forms are D-deoxynucleosides), their prodrug derivatives as .beta.-L-2' deoxythymidine (LdT) and .beta.-L-2'-deoxycytidine (LdC) are described in PCT patent applications WO00/09531 and WO 01/96353. these agents may readily be delivered using the hydrogels of the invention.

Bioactive agents as small molecules with nucleophilic groups include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, antispasmodic agents, anti-thrombotic agents, anti-tussive agents, anti-uricemic agents, anti-anginal agents, antihistamines, appetite suppressants, biologicals, cerebral dilators, coronary dilators, bronchodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other biologically active agents that can be included in the gels include androgen inhibitors, aminopolysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestyramine, N-acetylprocainamide, acetaminophen, aspirin, ibuprofen, phenyl propanolamine hydrochloride, caffeine, guaifenesin, peptides, polypeptides, proteins, amino acids, hormones, interferons, cytokines, and vaccines having nucleophilic groups.

The hydrogels may in other embodiments comprise peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids.

In yet another aspect, the implantable reporter hydrogels of the invention may be used for delivering a specific therapeutic or other agent to an external portion (surface) of a body passageway or cavity. Examples of body passageways include arteries, veins, the heart, the esophagus, the stomach, the duodenum, the small intestine, the large intestine, biliary tracts, the ureter, the bladder, the urethra, lacrimal ducts, the trachea, bronchi, bronchiole, nasal airways, Eustachian tubes, the external auditory mayal, vas deferens and fallopian tubes. Examples of cavities include the abdominal cavity, the buccal cavity, the peritoneal cavity, the pericardial cavity, the pelvic cavity, perivisceral cavity, pleural cavity and uterine cavity.

The release of the agents delivered by the reporter hydrogels is monitored using MRI techniques well known to those of skill in the art. In such techniques, the MRI apparatus induces a magnetic resonance phenomenon in the hydrogels that are placed in a static magnetic field by irradiation of the hydrogels with a high-frequency magnetic field at a particular frequency and acquires the physicochemical information of the measurement target. The MRI apparatus, which mainly utilizes the magnetic resonance phenomenon of the hydrogen nucleus in a water molecule, can image a difference in the density distribution or relaxation time of the hydrogen nucleus that differs among biological tissues. This can image a difference in tissue characterization and produces high effects in disease diagnosis. There are numerous conventional MRI apparatuses and their uses in imaging are well known to those of skill in the art.

In additional embodiments, the hydrogels described herein can be prepared with inactive precursor enzymes (zymogens) [55]. This will produce an enzymatic cascade. In exemplary embodiments, the zymogen used is trypsinogen, which is a zymogen secreted in the pancreas and is an inactive form of the serine protease trypsin [59]. Enterokinase, which is excreted in the duodenum activates trypsinogen to form trypsin, and trypsin further autocatalyses trypsinogen to form more trypsin, Thus, initiation of the activation cascade by enterokinase is very rapid and requires very little enterokinase. If trypsin is in the presence of proteins containing a specific peptide sequence (lys or asp resides), trypsin will cleave the protein, and will also lyse specific peptide sites in any surrounding proteins. In the present invention zymogens are embedded in reporter gels to make the degradation rates of the gels highly sensitive to target molecules for the zymogens. The rate of enzyme activity in the gel can be modeled using Michaelis-Mentin kinetics equations [60], and depends strongly on the concentration of zymogens embedded in the gel. In this manner very small (pM) concentrations of target enzyme (E.g., in this case enterokinase), can be used to create an enzyme-sensitive, degradable reporter gel with tunable sensitivity.

Exemplary zymogens that can be embedded in the reporter gels include but are not limited to trypsinogen, a chymotrypsinogen, a pepsinogen, a caspase, a proelastase, and a prolipase.

EXAMPLES

In the following Examples, there is provided a teaching of production and testing of reporter hydrogels. These reporter hydrogels described herein can be used in tissue engineering, drug delivery, or any application where strong biocompatible implant may be necessary. The desire for non-invasive diagnostic and prognostic information from implanted tissues will require this type of technology to maximize flexibility for design requirements of scaffolds for tissue engineering or drug delivery devices.

Example 1: Materials and Methods for Making Functionalized Nanoparticles

Ferritin is an iron storage protein expressed by mammalian cells, and contains up to 4500 iron atoms in its core. Ferritin is advantageous as a contrast agent in this application because of its small size (13 nm), which allows it to be strategically bound at distances on the order of inter-molecular spacing inside a gel. Because the relaxivity of native ferritin is limited by the amount of iron deposited in the core, we will make "magnetoferritin," with a modified protocol from that described previously [65-68].

Materials and Methods:

Magnetoferritin will be synthesized by adding iron chloride in a stepwise manner into a deaerated solution of apoferritin. 2 µM horse spleen apoferritin (Sigma Aldrich) in 0.05M MES buffer will be deaered with N2, by bubbling in the gas into the solution, apoferritin solution will be degassed for 15 minutes (pressure of 10 psi) before the first iron addition. Fe(II) Chloride will be diluted to 48 mM in 25 ml of deionized H2O, the flask will be covered immediately after preparation in order to avoid premature oxidation. Throughout the entire reaction, the apoferritin solution will be placed in a water bath at 58° C., and the iron solution will be placed and mixed on the hot plate deaering with N2 as well. Every 20 minutes, 62.5 µl of Fe(II) Chloride will be added to the apoferritin solution under N2 bubbling. The sample will be dialyzed against 15 mM NaCl. Once completely filled, magnetoferritin is expected to have a per-iron relaxivity of approximately 100 mM-1 sec-1, allowing ferritin to be detected in approximately 1 µM concentrations in the gel. This method has also been used to generate magnetoferritin (data not shown).

Magnetoferritin will be either cationized or otherwise functionalized to target specific ECM gel components. For cationization, DMPA will be cross-linked to magnetoferritin by the method of Danon et al [69]. The ferritin will then be dialyzed into PBS using Pierce dialysis cassettes. Protein concentrations will be measured spectrophotometrically by using a Bradford assay kit (BioRad, Inc). The relative electric charge will be determined by isoelectric focusing in a polyacrylamide gel.

To conjugate native ferritin to hyaluronic acid binding protein (HABP), biotinylated HABP and avidinferritin will be purchased from Sigma Aldrich and mixed to obtain a ratio of 24 HABP per ferritin monomer, or one HABP per ferritin subunit. To conjugate magnetoferritin to HABP, cationic magnetoferritin and avidin will be reacted with Sulfo-Kmus (Pierce, Rockville, Ill.) to form avidin-magnetoferritin. The avidin-magnetoferritin will then be mixed with biotin-HABP. Magnetoferritin will be characterized by transmission electron microscopy (TEM) as described below, and by inductively coupled mass spectrometry (ICPMS, West Coast Analytical Services, Santa Fe Springs, Calif.) for iron content, and MR relaxometry. Per-iron relaxivity of magnetoferritin will be determined using the Bruker 300 MHz Spectrometer, and by a Bruker 1.5 T and 0.5 T Biospin contrast agent analyzer/relaxomete.

The aggregation of SPIOs is known to change the transverse MRI relaxivity. The proposed reporter gels will rely on controlled aggregation of SPIOs to report on gel macromolecular structure. The inventors therefore tested whether aggregation could be controlled at the molecular level, and whether it could be used to report on the state of macromolecules bound to the SPIOs [53]. To test this, horse spleen ferritin nanoparticles were cross-linked at short distance (12 A) and measured its relaxivity compared to control (un-crosslinked) ferritin embedded in an agarose gel.

Figure 1B:
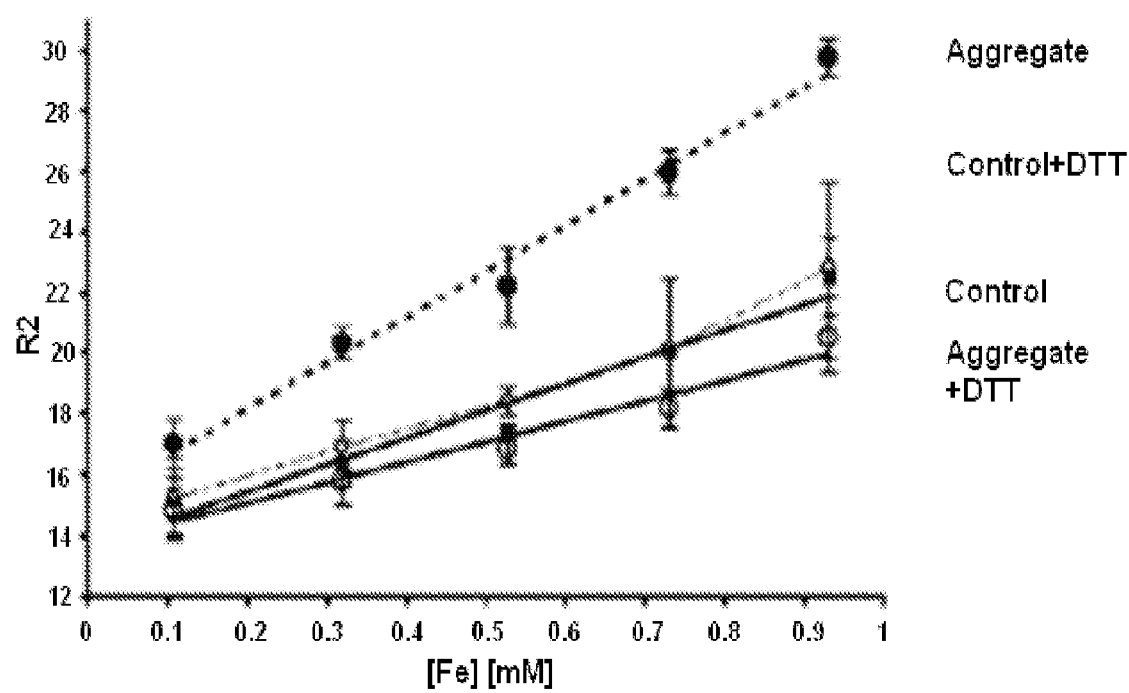

MRI was performed on the gels suspended in 1.5 ml Eppendorf tubes, using a Bruker 11.7 T scanner in a 35 mm ID birdcage RF coil, using a Carr-Purcell Meiboom Gill pulse sequence with TE/TR=6/3000 ms. As shown in FIG. 1, the relaxivity of crosslinked ferritin was approximately 70% higher than in un-crosslinked ferritin. This effect could also be reversed by chemically cleaving the crosslinker, demonstrating that the MRI signal could be modulated through aggregation and dis-aggregation of the SPIOs.

To determine whether the MRI signal could be modulated by letting ferritin aggregate in a biologically relevant in vitro system, we attached ferritin to unpolymerized G-actin and allowed the actin to polymerize in the presence of ATP. It was reasoned that the polymerization of ferritin-G-actin would cause a decrease in T2, similar to what we observed in the agarose gel. As shown in the same publication, the polymerization of actin from g- to f-form decreased T2 in solution. Furthermore, the MRI relaxivity was modulated by manipulating the inter-ferritin spacing within the aggregates, consistent with computational models of ferritin aggregation [53]. It is thus feasible to embed ferritin in biocompatible hydrogels to report on the polymerization status of the structural macromolecules to which the ferritin is bound.

Example 2: Materials and Methods for Creation of a Stable Line of DsRed-Expressing Cells The dsred-express-c plasmid DNA vector was purchased from BD Biosciences. Competent *e-coli* were transformed with the plasmid, and were grown in Luria broth with 30 ug/ml Kanamycin for selection. The DNA was recovered by Midi-prep (Qiagen) and run on a 1% agarose gel at 75 V (with 10 ul ethidium bromide in 100 ml agar) for two hours to verify the DNA size using a UV light source. C6 glioma cells were purchased from the American Type Culture Collection and grown in DMEM-F12 medium supplemented with fetal bovine serum and Horse serum, and 10 mg/ml of penicillin and streptomycin, at 37° C. with 5% CO2. Cells were plated and grown overnight to approximately 70% confluence. The growth medium was then replaced by serum-free medium for transfection. 20 ul of Lipofectamine 2000 (Invitrogen) were incubated with 250 ul serum free medium for 5 minutes in an Eppendorf tube. In a separate Eppendorf tube, 20 ul of the purified plasmid DNA was mixed with 250 ul serum-free medium. After this initial incubation, the DNA and Lipofectamine transfection reagent mixtures were combined and incubated at room temperature for 30 minutes. The mixture was then pipetted into the cell culture dish, and the cells were grown to confluence. and red fluorescence was observed in 90% of cells in the confluent dish after 48 hours using a Leica MZFLIII stereomicroscopy equipped with a Chroma dsred filter (Excitation/Emission wavelength: 546/450 nm). Cells were re-plated with growth medium containing no Pennicillin/streptomycin, supplemented with 600 ug/ml G418 for selection of cells containing the inserted plasmid. The cells were sorted by fluorescence activated cell sorting, in which only cells of the top 10% in fluorescence intensity were retained for further culture. These cells were then grown to confluence under selection and then taken for another round of FACS. In all, the cells underwent 6 rounds of FACS sorting. At this point, because stable fluorescence was observed with flow cytometry, the cells were plated onto a 96-well plate to obtain approximately 1 cell per 2 wells. Several single clonal colonies were then identified, grown to confluence, and then re-plated onto a single well of a 48-well plate, and then onto a T75 to obtain a clonal, high-level fluorescent cell line. The cells (approximately 106 per aliquot) were frozen in growth medium containing 5% DMSO, initially at −80° C. and then at −175 (in a liquid nitrogen freezer). The fluorescence is stable, and will be observed in cell progeny upon division. The same procedure will be carried out for the DU-145 cells.

The fluorescence of this cell line is stable and will be observed in all cell progeny upon division. It will be used for all C6 glioma experiments proposed, and will allow detection of the cells in culture dishes invading into three-dimensional reporter gels.

Example 3: Materials and Methods for Nuclear Magnetic Resonance and Magnetic Resonance Imaging Nuclear magnetic resonance (NMR) and MRI will be performed to measure the static field susceptibilities and in vitro relaxivities of the reporter gels in vitro and in vivo. For in vitro experiments, a 400 MHz Varian NMR spectrometer with a 10 mm liquids probe will be used. To measure the relaxivity of MCF, MCF will be injected into a glass capillary and flame sealed. The capillary will be inserted into a volume of 10% $D_2O$ and 90% $H_2O$. The $D_2O$ signal will be used for spin-locking, and the offset between the $H_2O^1H$ main and secondary peaks will be computed, from which the static susceptibility of the sample will be determined. To measure the relaxivity of reporter gels before and after proteolytic degradation, 5 mm ID NMR tubes will be filled with 500 ml of each sample (containing 10% $D_2O$) on ice and inserted into the NMR probehead and maintained at 35° C. to solidify the gel. The proton spectrum will be acquired, and the amplitude of the main peak and associated T2 relaxation rate will be obtained using a CPMG pulse sequence. T2 will be measured every 30 minutes after gelling with and without proteolytic enzymes, for up to 24 hours.

In vivo and cell culture MRI will be done on both a Varian vertical 89 mm wide-bore 300 MHz system equipped with three-axis imaging gradients and a gradient ID of 50 mm, using a Doty linear surface coil with a butterfly surface transmitter, or with a Bruker 7 T scanner housed at the Barrow Neurological Institute (Phoenix, Az), which is due for installation in May 2008. For combined MRI and microscopy, gels will be loaded into cell culture dishes and inserted into a 75 mm diameter quadrature volume resonator and imaged using a rat brain quadrature surface coil equipped for active decoupling. Pilot T2-weighed gradient-echo scans will be used to localize the region of interest, and axial (transverse) slices of 500 µm×500 µm×1 mm will be acquired using a fast gradient-echo (FLASH) sequence with TE/TR=20/200 ms. For in vivo MRI, mice will be anesthetized with a 30% oxygen/70% nitrogen (oxygen-enhanced air) gas mixture containing 5% isofluorane by nosecone, then either intubated and ventilated with the same air/gas mixture with 2-5% isofluorane, or placed under nosecone in the MRI holder for imaging. Rectal temperature will be maintained at 37° C. by temperature-controlled warmwater blanket. The surface RF coil will be placed over the flank and imaged using both a fast gradient echo sequence (TE/TR=20/200 ms) and a CPMG sequence (TE/TR=10-20/200 ms) to measure T2. In both cases, spatial resolution will be 500 µm×500 µm×1 mm, with a total of 3-5 slices to cover the gel. After the final scan series, the reporter gel will be surgically resected for microscopy and the animal will be sacrificed.

Example 4: Materials and Methods for Microscopy

Light Microscopy.

For fluorescence microscopy, gels and gross histological sections will be fixed in 4% paraformaldehyde in 3% BSA, frozen, and sectioned at 20 mm thickness. The sections will be rinsed 2× with Dulbecco's Phosphate-Buffered Saline (DPBS). Anti-horse spleen ferritin (Sigma-Aldrich, St. Louis, Mo.) will be applied to sections in DPSS with 1% BSA for 1 hr at 25° C. The sections will be washed 3× with NPM or DPSS. The secondary antibody, Alexa Fluor 594 or 488 anti-rabbit IgG (Invitrogen, Carlsbad, Calif.), will be applied in the same manner. In cell experiments, DAPI will be used to counterstain the cell nuclei by applying a 1 µg/ml DAPI solution for 10 min. The slides will be rinsed with 1% BSA. Fluorescence images will be acquired on a Leica DM IRBE fluorescence microscope with an Optronics 750D camera in the ASU Bioengineering core microscopy facility, and laser scanning confocal microscopy will be performed at the ASU School of Life Sciences Keck imaging facility. Optical emissions filters cover the dsRed emission spectrum.

Electron Microscopy.

To characterize filling of SPIOs, magnetoferritin will be adsorbed to carbon-coated grids and imaged with a Phillips EM 201 microscope at the ASU core electron microscopy facility to confirm iron filling in the core. Gels and tissue samples will be prepared for electron microscopy by fixation with 1N cacodylate buffer and 2% gluteraldhyde, Selected areas will be trimmed, dehydrated with a graded series of ethanol mixtures, infiltrated with graded mixtures of ethanol and epoxy resin (SPI Supplies; West Chester, Pa.), and embedded in epoxy resin. Polymerization of the resin will be carried out at 60° C. for at least 48 hours. All Images will be taken with a Phillips EM 201 transmission electron microscope.

Example 5: Materials and Methods for Creating Biologically Derived Reporter Gels Biologically derived ECM gels have the advantage of containing molecules present in ECM throughout the body, and therefore have the potential to interact with cells to direct migration. Furthermore, FDA-approved ECM gels are available, making clinical translation of reporter gels feasible. High-density Matrigel® (BD biosciences) will be suspended 1:1 in dH2O, with either native or cationic magnetoferritin NMF or CMF, with ferritin concentrations ranging from 1-10 µM. Because CMF binds to charged glycosaminoglycans, it will be polydisperse (aggregated) and the NMF will remain monodisperse (unaggregated).

Magnetic Resonance Methods:

Transverse relaxation measurements will be made on a Bruker 60 MHz and a 20 MHz Minispec contrast agent analyzer (Bruker Optics, The Woodlands, Tex.). A CPMG pulse sequence with TE/TR=0.06/10.0 s will be used. Sample temperature will be maintained at 37° C. through the temperature-controlled 1H RF probe, and gels will be maintained at the same temperature by a tempering block when measurements are not being taken. 10 measurements will be averaged. T2 will be computed by fitting the CPMG curve to an exponential function using Matlab, (The Mathworks, Inc, Natick, Mass.).

Electron Microscopy:

TEM will be performed on NF- and CF-matrigel to determine inter-particle distance and to estimate SPIO spacing in the gel. All TEM will be done on fixed sections of the gel.

Analysis Methods:

Transverse relaxivity will be compared between samples using a two-tailed student's t-test, and differences will be considered significant if $p<0.05$, with a statistical power of 0.9.

Alternative Approaches:

Although magnetoferritin with improved T2 relaxivity has been reported by several groups, it is possible that the relaxivity of magnetoferritin will be insufficient to modulate the gel relaxivity for specific gel macromolecular concentrations. In this case, commercially-available SPIOs functionalized in the same way also may be used as an alternative (Biopal, Inc, Worcester, Mass.).

This example demonstrates that ferritin can be targeted to specific, biologically relevant components of the extracellular matrix (ECM). As a model, the inventors targeted basement membrane proteoglycans, which contain multiple negatively charges SO4 groups. Cationic (amine-coated, positively charged) ferritin was injected intravenously into male Sprague Dawley rats and allowed to accumulate in the kidney glomeruli [61]. Native (non-cationic NF) nanoparticles were delivered as a control. CF was taken up into the basement membrane of the glomeruli, while NF was not, and the accumulation of CF in the glomeruli at approximately 50 µM was detected using gradient-echo MRI. The presence of CF was confirmed using immunofluorescence and transmission electron microscopy, and demonstrated that the charged particles, but not the native particles, specifically accumulated in the basement membrane. This demonstrates the feasibility of detecting the aggregation of nanoparticles in vivo, and shows that cationic nanoparticles can be used for highly specific targeting of ECM components.

These results show that MRI reporter gels can be detected in vivo, because the reporter gels will contain nanoparticles in similar concentrations to those used in this example.

Example 6: Materials and Methods for Digestion of Biologically Derived Reporter Gels by Proteolytic Enzymes Trypsin and Heparinase I Data presented below show that MRI reporter gels are degraded by proteolytic and glycolytic enzymes, and that this degradation is detectable with MRI. Trypsin, a serine protease, is known to cleave arg and lys residues on proteins, and is thus expected to digest the protein structure of heparin sulfate proteoglycans in the gel, leaving the glycan groups intact but separated from the protein. Heparinase I cleaves carbohydrate groups at the linkage sites of sulfated iduronic acids and hexosamines, and should thus break down the entire carbohydrate chain but leave the protein core intact. By measuring changes in MRI relaxivity of reporter gels during degradation with these two specific enzymes, we will determine the specificity of the reporter gels. To verify that changes in the MRI signal are a direct result of enzyme activity, fluorescence microscopy of a fluorescent marker of enzyme activity can be performed as shown herein.

Materials and Methods:

Porcine pancreatic trypsin and Flavobacterium heparinase I will be purchased from Sigma Aldrich (Sigma, St Louis, Mo.). 400 ml Matrigel (BD Biosciences) will be mixed with 100 ml 0.1 M Tris buffer, pH 7.4 (control), or the same Tris buffer with enzyme (Trypsin or Heparinase I) in 7 mm NMR tubes on ice. The enzyme concentrations will be varied from 50 to 200 units per total volume. CF and NF, suspended in 7.4 pH saline in 0.5-20 µM concentrations in the gel. Gels with the same volume of saline but no NF or CF will be used as a control.

MR Methods:

Transverse relaxivity measurements will be made on a Bruker 1.5 T and a 0.5 T Minispec contrast agent analyzer (Bruker Optics, The Woodlands, Tex.), currently housed in the PI's lab. A CPMG pulse sequence with TE/TR=0.06/10.0 s will be used, with measurements made every two hours during gel degradation. Sample temperature will be maintained at 37° C. through the temperature-controlled 1H RF probe, and gels will be maintained at the same temperature by a tempering block when measurements are not being taken. Measurements will be taken every 2 hours. 10 measurements will be made at each time point. T2 at each of these timepoints will be computed by fitting the CPMG curve to an exponential function using Matlab, (The Mathworks, Inc, Natick, Mass.).

Light and Electron Microscopy:

We will use an EnzCheck protease assay kit (Invitrogen, Carlsbad, Calif.) employing the BODIPY fluorescent dye to detect the activity of trypsin in reporter gels. The assay employs a fluorogenic substrate that increases in fluorescence intensity with activation by the enzyme. The substrate will be suspended in the reporter gel when it is still liquid, and incubated. Because the enzyme causes a 10-20% change in fluorescence intensity with 100 units of enzyme in excess of substrate, the substrate should be able to detect the enzyme in quantities used in this work. During digestion, fluoroescence intensity will be measured every 2 hours with a Leica Axioplan fluorescence microscope in the ASU Bioengineering core microscopy facility, with a fixed exposure time across measurements. Heparinase I activity will be assessed using a heparinase assay kit (CisBio, inc, Bedford, Mass.) in the same way. To determine gel structure after digestion, TEM will be performed on fixed gel samples, as described herein.

Data Analysis:

Changes in T2 between control and enzyme-digested samples will be determined using a paired students t-test. Differences will be considered significant if $p<0.01$.

Alternative Approaches:

The change in MRI relaxivity with aggregation is sensitive to the concentration of CF or NF. If the relaxation change is insignificant at this concentration, we will increase the concentration. The field strength can also affect the relaxivity, and we will make relaxivity measurements on high-field (9.4 T, 18 T) NMR equipment available in the Magnetic Resonance Center at ASU. In the event that the proposed enzymes do not fully digest the gels, Heparinase III, hyaluronidase, can be used since both cleave components of macromolecules present in matrigel.

Figure 2A:
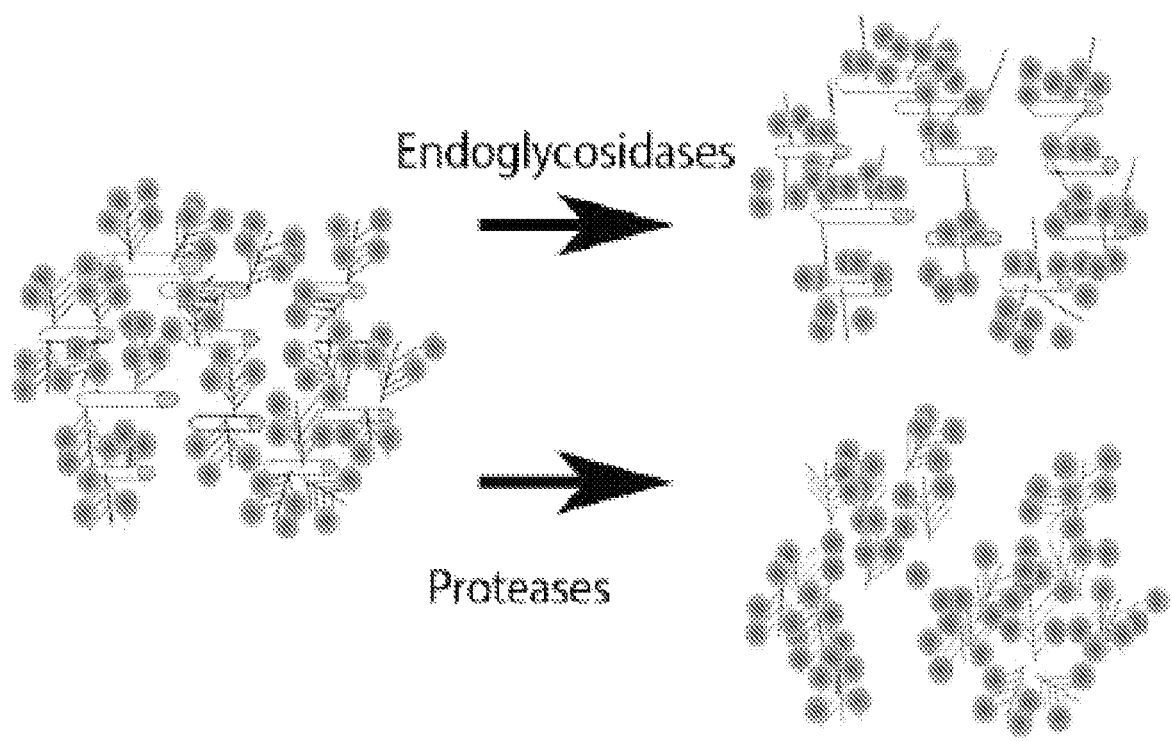
FIG. 2: Illustration (left) and experiments (right) showing controlled aggregation of functional SPIOs in a reporter gel with degradation by specific enzymes. Thin lines represent structural proteins and glycans, and aggregation depends on the specific enzyme used. (a,b) TEM native (a) and cationic (b) ferritin in matrigel. Native ferritin is monodisperse, while cationic ferritin aggregates due to negatively charged macromolecules in the gel. (c,d) Light microscopy shows the same effect: matrigel is clear (c), while cationic ferritin in matrigel is turbid (d) and aggregates are visible. (e) matrigel-CF reporter gel after digestion with trypsin, and (f) after digestion with heparinase I, showing that the bulk structure of the gel depends on the enzyme.
Figure 2B:
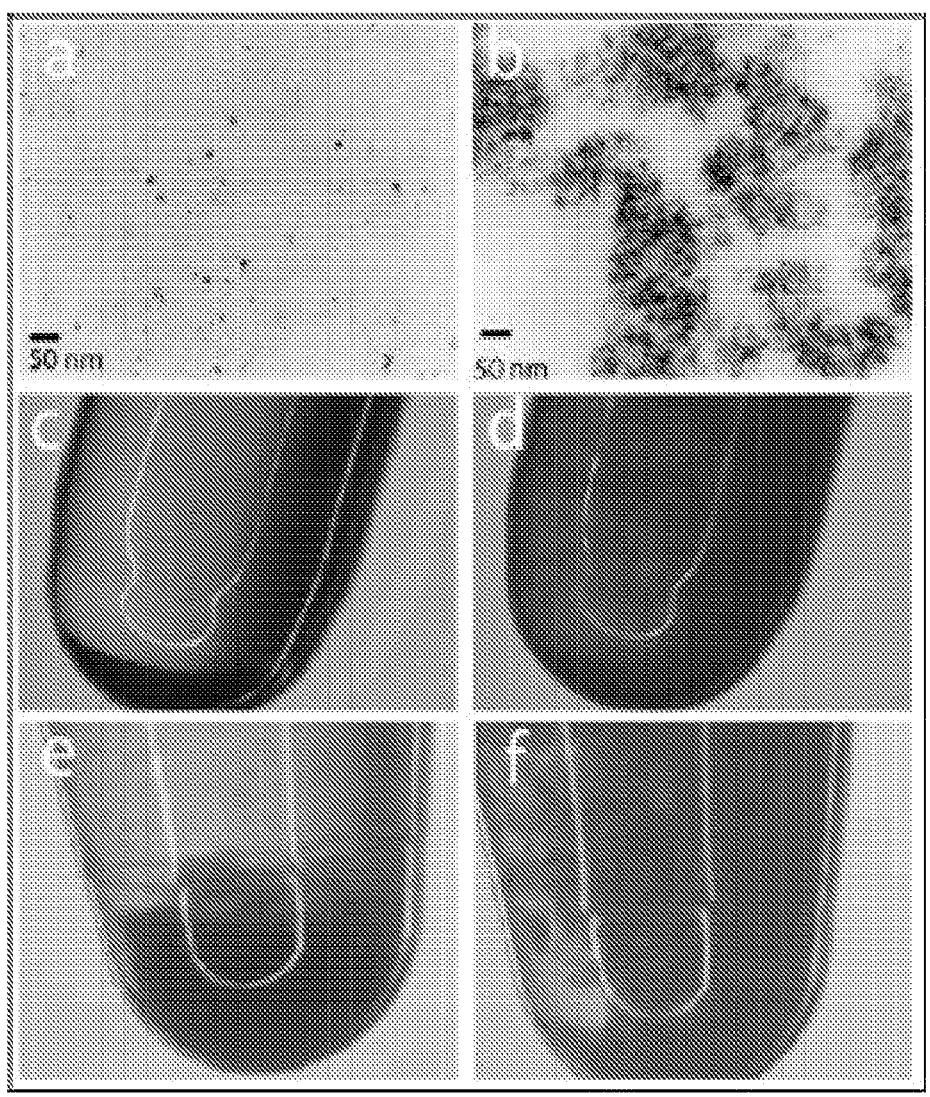

Thus, in preliminary experiments, in order to determine whether MRI could be used to detect the molecular structure and breakdown of an ECM gel, Matrigel® (BD Biosciences) was doped with NF or CF in liquid state. To determine whether the structure of the reporter gels during degradation could have specificity to the type of degrading enzyme, samples of Matrigel containing 1 µM CF and NF were suspended with 10 µM trypsin or heparinase I and incubated at 37° C. for 24 hours. The gels were examined with transmission electron microscopy and light microscopy. As seen in FIG. 2, The CF bound to negatively charged ECM components, including glycosaminoglycan chains, causing CF to aggregate. By contrast, NF was uniformly distributed in the gel, and was monodisperse in TEM. The gels were degraded by both trypsin and heparinase I, but the macromolecular structure in the gels was clearly different depending on the enzyme used to degrade it. In the case of trypsin, the gel collapsed and caused aggregation of the proteoglycan-bound CF to the bottom of the tube. In the case of heparinase I, the gel structure remained intact but cause aggregation of CF into small clusters.

Figure 3:
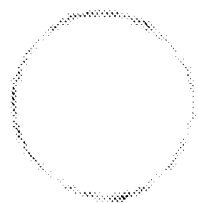
FIG. 3: Gradient-echo MRI of matrigel plugs doped with either NF or CF, in the absence or presence of serine protease (trypsin).
Figure 3:
Figure 3:
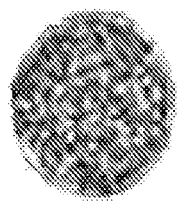
Figure 3:
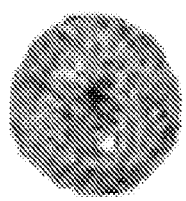

To determine whether proteolytic degradation of the gels could be detected with MRI, samples of the trypsin-digested gels were imaged in Eppendorf tubes using a Bruker 11.7 T scanner with a 35 mm ID birdcage RF coil, using a spoiled gradient-echo pulse sequence with TE/TR=10/500 ms. As shown in FIG. 3, the T2*-weighted signal intensity was modulated by the structure of the gel. The signal intensity in the NF-doped gel was 150% higher than in the gel containing CF, indicating that CF was aggregated by electrostatic binding to closely-spaced glycosaminoglycans. Differences were statistically significant (p<0.05). When trypsin was added to the gel, the signal intensity in the sample became heterogenous, with a range between that of the NF- and the CF-doped gel. This was consistent with gel degradation observed with light microscopy. When trypsin inhibitor was added, signal intensity was uniform, but higher than in the CF-doped gel, suggesting only partial degradation of the gel. These results supports the hypothesis that the relaxivity of reporter depends on the distribution of its structural molecules before and after enzymatic degradation.

Example 7: Materials and Methods for Demonstrating Cellular Migration into the Biological Reporter Gels This example may be used to determine the sensitivity of reporter gels to cellular breakdown of the ECM. Migrating cells are known to remodel ECM macromolecules both in vitro and in vivo. Therefore, an invasion assay may be used to study the changes in MRI relaxation that occur when invasive C6 glioma cells migrate through the gels. As a negative control, we will also measure MRI in a model of a noninvasive DU-145 cell line. This will test the ability to detect cellular migration into reporter gels when they are implanted.

Materials and Methods:
To determine the effects of cell migration on reporter gel structure and MRI relaxivity, highly invasive C6 rat, and a noninvasive line of DU-145 human prostate carcinoma cells will be plated on the biologically derived and synthetic gels. The DU-145 cell line has been previously shown to have limited invasion in a Boyden chamber assay [70]. Both cell lines will stably express dsred for visualization with light microscopy. The cells will be seeded at a density of $10^4$-$10^5$ cells per $cm^2$ onto the gel surface, allowed to attach, bathed in respective growth medium, and incubated at 30° C. with 5-10% $CO_2$, for between 2 days to 1 month. A control gel containing no cells will also be plated for comparison in fluorescence microscopy.

Fluorescence Microscopy:
Fluorescence microscopy will be used to determine whether cells have entered the gel and, if so, at what density. Images will be taken using a rhodamine filter.

MRI Methods:
Transverse MRI relaxation time will be measured using a 3 T GE whole-body human MRI housed at the Keller Center for Imaging Innovation at the Barrow Neurological Institute, or by the 7 T Bruker 30 cm Pharmascan. Rectangular dishes containing the matrigel samples will be imaged using both gradient echo and spin-echo.

Data Analysis:
In fluorescence microscopy, cell density will be determined by fluorescence intensity of the gels containing cells, compared to those that do not, with images taken at the bottom of the dish (which should contain no cells when first plated). In MRI, differences in T2 and T2*-weighted images will be compared using a two-tailed Student's t-test. Differences will be considered significant if p<0.05, with a statistical power of 0.9.

Alternative Approaches:
The focal length of the stereomicrocscope will be adjusted to a plane away from the top of the culture dish. However, it is possible that emitted light from cells at the top of the Matrigel® cause the camera to saturate, and make it impossible to determine the actual fluorescence intensity. In this case, samples of the gel can be excised, digested with a matrigel removal kit (BD Biosciences), and perform flow cytometry to determine the density of cells in a specific volume of gel, allowing us to compare between invasive C6 and noninvasive DU-145 cells.

Example 8: Materials and Methods for Development of a Zymogen Cascade Amplifier to Improve Reporter Gel Sensitivity In reporter gels, the rate of gel digestion and MRI signal changes depend on the concentration of proteolytic enzymes or cells in the gel. For larger gels necessary for implantation, the entire volume of an MRI voxel must be filled with the proteolytic enzyme, typically at 1 µM, for detection, as seen in the findings shown herein in Matrigel® digestion with trypsin. To better understand the zymogen cascade, the process may readily be mathematically modeled to determine the required enzyme concentrations.

Materials and Methods:
Biological reporter gels will be developed as described herein 1, except that 100 nM-10 µM trypsinogen will be added to the gel before solidification. The gels will be incubated at 40° C. for up to 48 hours.

Light Microscopy:
The EnzCheck protease assay kit (Invitrogen, Carlsbad, Calif.) will be used to detect the activity of trypsin in reporter gels embedded with zymogens. This will directly test trypsin activity in the gel, which is a measure of activation by enterokinase. Digestion of the reporter gels embedded with zymogens will be visualized by light microscopy, and verified by TEM to determine CF spacing in the gel.

Mathematical Modeling:
The reaction kinetics of a self-activating protease can be described by the first-order differential Michaelis-Mentin equation. This equation describes the change in zymogen concentration as a function of starting concentration and known reaction rates. The reaction rates for trypsinogen will be determined by light microscopy for trypsin activity, as described above. The equations can be modeled using Matlab, and the initial concentration of enterokinase required will be computed based on the total amount of trypsinogen in the sample.

MR Methods:
Transverse relaxivity measurements will be made on a Bruker 1.5 T and a 0.5 T Minispec contrast agent analyzer (Bruker Optics, The Woodlands, Tex.), currently housed in the PI's lab. A CPMG pulse sequence with TE/TR= 0.06/10.0 s will be used, with measurements made every two hours during gel degradation. Sample temperature will be maintained at 37° C. through the temperature-controlled 1H RF probe, and gels will be maintained at the same temperature by a tempering block when measurements are not being taken. Measurements will be taken every hour. 10 measurements will be made at each time point. T2 at each of these timepoints will be computed by fitting the CPMG curve to an exponential function using Matlab, (The Mathworks, Inc, Natick, Mass.).

Alternate Approaches:
The Examples herein have verified that activated gels (exposed to enterokinase) are digested within only 4 hours. A limitation to this approach is that it only tests a single zymogen, making it unclear how the technique could be applied in a synthetic system. An alternate approach is to suspend an activating enzyme in the gel which is conjugated to a peptide with a specific binding site for a target enzyme (e.g. a matrix metalloproteinase). This enzyme, once freed from the gel, activates the zymogen cascade. Thus, it will be possible to make the zymogen cascade applicable to synthetic reporter gels.

Figure 4:
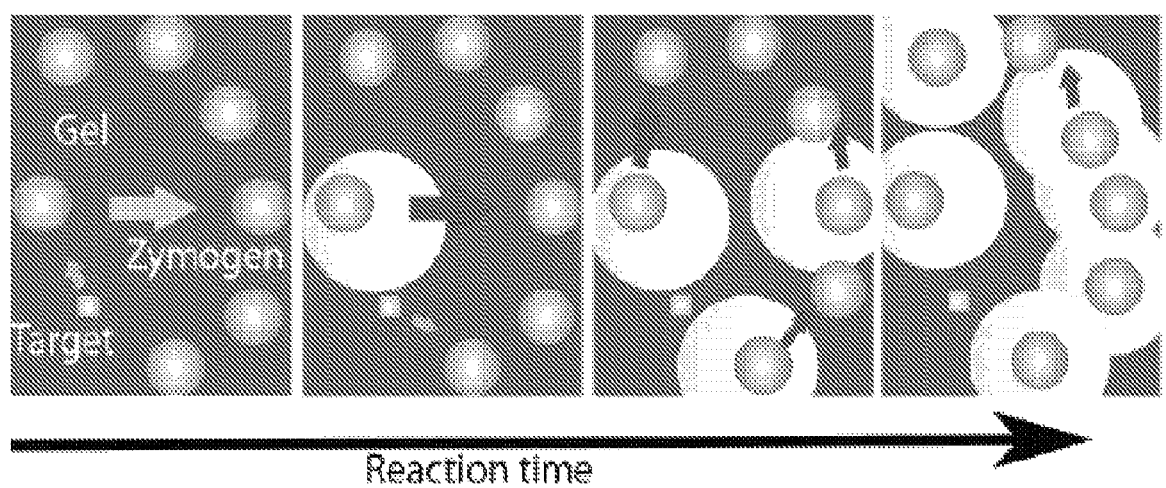
FIG. 4: Schematic illustration of a zymogen cascade to degrade a reporter gel. The reporter gel is shown as the brown background. When the target enzyme activates gel-embedded zymogens, these activated enzymes both digest the gel and activate other zymogens, amplifying the digestion of the gel.

The purpose of this preliminary study was to determine whether enzymatic cascades can be used to amplify the sensitivity of reporter gels to target molecules. A simple zymogen cascade was developed to assess this, based on the activation of trypsinogen to trypsin by enterokinase. Upon activation, trypsin was expected to activate more trypsinogen, initiating a rapid degradation of the gel by trypsin. Because the gel was doped with the CF nanoparticles bound to charged proteoglycans, the degradation of the gel was expected to be MRI—detectable when the proteoglycans were cleaved. A schematic of the process is shown in FIG. 4.

High-density matrigel (BD Biosciences) was thawed at 40° C. and mixed with 25% PBS and 1 µM cationic ferritin nanoparticles and 2 µM trypsinogen (Sigma Aldrich) and kept on ice. Varying amounts of enterokinase (from 0 to 1 nM) were added, and enterokinase buffer (TRIS) was added to each tube to keep the total gel volume and all other conditions constant. The gel was loaded into a 10 mm ID NMR tube and incubated at 37° C. to solidify the gel and initiate enzyme activity.

Figure 5:
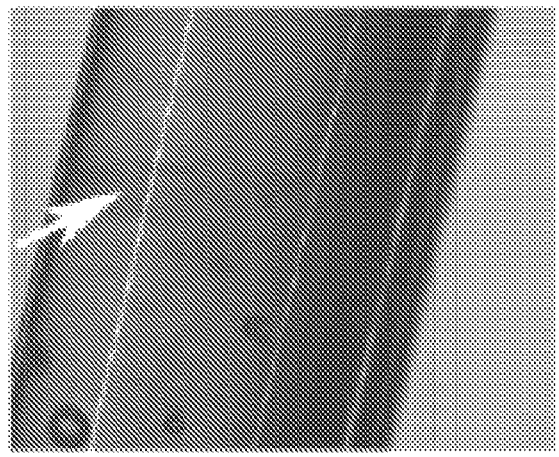
FIG. 5: Stereomicroscopy of matrigel reporter gel with 2 µM trypsinogen zymogen and either control buffer (left) or 4 pM enterokinase (right). Cationic ferritin bound to the gel macromolecules gives visible contrast of the gel when it is undigested (in control, left), but shows that the gel is completely degraded in the presence of enterokinase (right).
Figure 5:
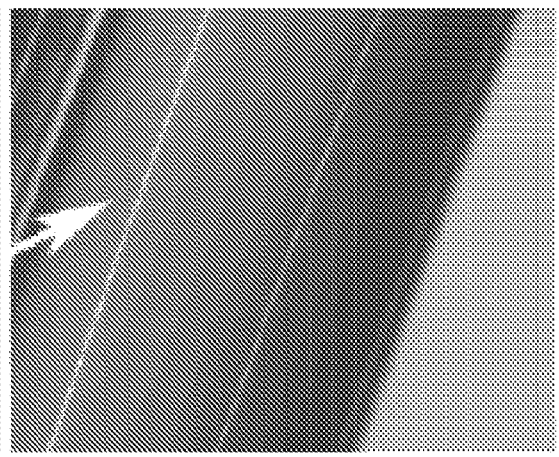

As shown in FIG. 5, the gels with the activating enterokinase were visibly degraded after 4 hours, but the controls (with no enterokinase) were not, consistent with activation of the zymogen cascade by the enterokinase. Gels with and without enterokinase were completely degraded, and were indistinguishable, after 2 days, indicating background activity of trypsinogen conversion to trypsin. However, the rate constant for gel degradation with enterokinase was estimated to be five times greater than without. These results support the finding that the rate and sensitivity of reporter gel degradation can be enhanced through an enzymatic cascade.

Example 9: Materials and Methods for Creating Synthetic Reporter Gels

The present invention shows that biocompatible materials can be prepared that can be studied noninvasively after implantation in humans. Many implanted materials are formed from synthetic polymers which are relatively biologically inert, making it imperative that the reporter gel strategy can be applied to detect the structure of synthetic molecules noninvasively. To this end, it is possible to create a synthetic polymer from either polyacrylic acid (PAA) or hyaluronic acid (HA), crosslinked with dextran and conjugated to MRIdetectable SPIOs. By conjugating the SPIOs to either dextran or HA, the changes in the synthetic gel structure can be determined in response to specific dextranase or hyaluronidase enzymes in vitro and in vivo.

Materials and Methods:

Electrospun dex-PAA fibers and other dextran polymers which are known in the art for coatings and tissue adhesion. [71-73] These components can be used in the reporter gels. Since electrospun dex-PAA fibers dissolve when immersed in aqueous solution, an intrafiber crosslinking reaction is performed to maintain aqueous stability. The —OH and —COOH groups of dextran and PAA, respectively, are advantageously used in an esterification reaction to form ester bonds between dextran and PAA. Crosslinking density is controlled by the mer ratio of dextran:PAA, which sets the number of PAA —COOH groups available to react with dextran —OH groups. At sufficiently high cross-linking density, fibers remain stable in aqueous solution and swell to become hydrogel fibers. Because of the negatively charged —OH and —COOH groups of dextran on the fibers, CF will be adsorbed directly to the fibers. Additionally, fibers will be mixed with 2% hyaluronic acid on ice, then CF-HABP or NF-HABP (using magnetoferritin) will be mixed for a total concentration of 100 nM to 10 µM.

MR Methods:

Transverse relaxation measurements will be made on a Bruker 1.5 T and a 0.5 T Minispec contrast agent analyzer (Bruker Optics, The Woodlands, Tex.). A CPMG pulse sequence with TE/TR=0.06/10.0 s will be used. Sample temperature will be maintained at 37° C. through the temperature-controlled 1H RF probe, and gels will be maintained at the same temperature by a tempering block when measurements are not being taken. 10 measurements will be averaged. T2 will be computed by fitting the CPMG curve to an exponential function using Matlab.

Electron Microscopy:

TEM will be performed on NF- and CF-bound PAA and HA-reporter gels to determine inter-particle distance and to estimate SPIO spacing in the gel. All TEM will be done on fixed sections of the gel, as described herein above, and also by adsorbing the fibers to a carbon grid before solidification.

Analysis Methods:

Transverse relaxivity will be compared between samples using a two-tailed student's t-test, and differences will be considered significant if p<0.05, with a statistical power of 0.9.

Alternative Approaches:

There are many alternatives to the synthetic gels used here. If the PAA- or HA-gels fail to serve as reporter gels, we will pursue a PEG hydrogel. The basic gel will consist of polyethylene glycol (PEG) polymer chains crosslinked to SPIOs, which will have an MMP-specific peptide shared with another PEG cluster. Crosslinking will be accomplished using a heterobifunctional crosslinker containing a maleimide on one end and a succinimidyl ester on the other for crosslinking to the peptide (Pierce, Rockville, Ill.). Upon introduction of activated MMP (MMP1, Calbiochem) to the gel, the peptide will be cleaved and allow the individual PEG gel components to detach from the network, causing the gel to liquefy. This will change the relaxivity of the gel by changing the aggregation state of the MCF, which will be detectable by MRI.

For in vivo implantation, a neurotrophic factor (BDNF) or hyaluronic acid, will be added to the gel to promote neurite and astrocytic growth.

In preliminary studies the development of precisely controlled nano- and micro-fibers as scaffolds for SPIOs, which could themselves be embedded in a biocompatible matrix for delivery was demonstrated. These scaffolds are comprised of dextran and polyacrylic acid (dex-PAA) polymer blends. Dry fibers have been created by electrospinning, with diameter ranges between 100 nm and 850 nm. These morphological properties depend on electrospinning conditions [62-64]. In this work, fiber diameters were controlled by varying electrospinning solution properties: (1) polymer concentration and (2) molecular weight (MW) of component polymers. Smaller diameter fibers with resulted from electrospinning lower concentrations/lower MW polymer solutions, while larger diameter fibers resulted from electrospinning higher concentrations/higher MW polymer solutions. The effect of solution concentration on fiber diameter and morphology is shown by SEM images of dry dex-PAA fibers. Because the electrospun fibers are negatively charged, cationic SPIOs (CF) bind readily to them, and native, uncharged SPIOS (NF) do not, as verified by darkening of the fibers after incubation with SPIOs (data not shown). These results demonstrate the feasibility of creating synthetic reporter gels that are biocompatible and able report on macromolecular gel structure.

Example 10: Materials and Methods for Detecting Synthetic Gel Structure after Digestion with Hyaluronidase and Dextranase Synthetic reporter gels will contain either dextran or hyaluronic acid bound to CF or NF. The ability of reporter gels to report on gel degradation by dextranase or hyaluronidase will be detected, to determine the sensitivity of the gels after they are implanted in vivo.

Materials and Methods:

For hyaluronidase digestion, synthetic gels will be prepared as described above and placed in 15 ml of 0.2 M sodium phosphate buffer containing 50 U of hyaluronidase (Sigmal Aldrich). CF and NF, suspended in 7.4 pH saline in 0.5-20 µM concentrations in the gel. Gels with the same volume of saline but no NF or CF will be used as a control. Samples will be incubated at 37° C. for times adequate to see degradation of the samples. For dextranase samples, the reporter gels will include 5 mM citrate buffer, pH 6.0, containing 1 unit per ml dextranase, and incubated at 37° C.

MR Methods:

Transverse relaxivity measurements will be made on a Bruker 1.5 T and a 0.5 T Minispec contrast agent analyzer (Bruker Optics, The Woodlands, Tex.), currently housed in the PI's lab. A CPMG pulse sequence with TE/TR=0.06/10.0 s will be used, with measurements made every two hours during gel degradation.

Sample temperature will be maintained at 37° C. through the temperature-controlled 1H RF probe, and gels will be maintained at the same temperature by a tempering block when measurements are not being taken.

Measurements will be taken every 2 hours. 10 measurements will be made at each time point. T2 at each of these timepoints will be computed by fitting the CPMG curve to an exponential using Matlab, (The Mathworks, Inc, Natick, Mass.).

Light and Electron Microscopy:

The PAA- and HA-reporter gel fiber structures are easily visualized with light microscopy (30× objective). Additionally, FITC-conjugated fibers have been created and can be visualized by fluorescence microcopy. Both of these techniques will be used to confirm the action of the enzymes on degrading the synthetic hydrogel. To determine gel structure after digestion, TEM will be performed on fixed gel samples, as described above.

Data Analysis:

Changes in T2 between control and enzyme-digested samples will be determined using a paired students t-test. Differences will be considered significant if $p<0.05$, with a statistical power of 0.9.

Alternative Approaches:

The change in MRI relaxivity with aggregation is sensitive to the concentration of CF or NF. If the relaxation change is insignificant at this concentration, the concentration should be increased. The field strength can also affect the relaxivity, and relaxivity measurements will be made on high-field (9.4 T, 18 T) NMR equipment available in the Magnetic Resonance Center at ASU. In the event that the proposed enzymes do not fully digest the gels, other enzymes, e.g., Heparinase III, hyaluronidase, can be used since both these enzymes specifically cleave components of macromolecules present in Matrigel®.

Example 11: Materials and Methods for Detecting Synthetic Gel Degradation In Vivo in a Rat Model of Spinal Cord Injury Using MRI Spinal cord injuries are among the most common, debilitating injuries, and synthetic tissues have been developed to guide neurons in the injury site and to re-establish nerve function. Hyaluronic acid is known to facilitate cell movement into a spinal cord injury in rats, and can be implanted as a biocompatible gel into the site of injury. Currently, there is no noninvasive method for detecting cells when they move through the gel noninvasively, and it is therefore impossible assess the efficacy of specific gels in guiding cells into them. Therefore, implanted hyaluronic-acid based reporter gels prepared in accordance with the invention can be used to detect when cells move through the gel. The following example teaches how exemplary such reporter cells can be used Materials and Methods:

A total of 60 rats will be anesthetized with a 30% oxygen/70% nitrogen (oxygen-enhanced air) gas mixture containing 5% isofluorane by nosecone. Under sterile conditions, T_10 laminectomy will be performed. In the control/experimental groups, a lateral hemi-section of the left spinal cord will be performed at T_9-10. Approximately 30 ml of either the biologically derived (30 rats) or artificial reporter gel (30 rats) will be injected into the cavity, with a total volume of 2000-3000 mm3.

Magnetic Resonance Imaging:

Magnetic resonance imaging will be performed at 2, 7, and 14 days after gel implantation. Animals with gels containing unfunctionalized nanoparticles or no nanoparticles will be used as controls. The site of injury will be localized by visualization of the vertebrae in a scout three-plane spoiled gradient echo pulse sequence, and T2 and T2*-weighted imaging will be performed as described above.

Fluorescence Microscopy:

To detect the growth of cells into the gel relative to nanoparticles using ex vivo fluorescence microscopy, each rat will receive a laminectomy at T_11 two hours prior to sacrifice. Sacrifice will take place at the same time-points as MRI, so that fluorescence can be correlated with MRI. The fluorescent membrane dye DiI (Invitrogen) will be injected into the spinal cord at T_3, and allowed to be taken up by neurons downstream of the injection. The dye is expected to be taken up into the implanted gel when cells grow into it.

Data Analysis:

Fluorescence intensity will be quantified by comparing images after DiI injection at each time point using Photoshop software (Adobe, Inc, San Jose Calif.), and compared to changes in T2 and T2* in MRI. Changes between time points in both MRI relaxation times and fluorescence intensity will be considered significant if $p<0.05$, with a statistical power of 0.9 in a two-tailed Student's t-test.

Alternative Approaches:

It is possible that the synthetic reporter gels do not elicit neurite regrowth in the spinal cord. In this case, we will pursue a subdermal implant of both gels. Such subdermal implants are known to be modified by cell proliferation, and are a common model for tissue biodegradability [74].

In preliminary studies in order to test reporter gels in vivo, and to determine if cells invading into synthetic reporter gels can be detected with MRI, a rat spinal cord hemisection was developed. The goal of these preliminary studies was to assess detection of the spinal cord in the model using MRI.

Two rats were anesthetized with a 30% oxygen/70% nitrogen (oxygen-enhanced air) gas mixture containing 5% isofluorane by nosecone, and a T_10 laminectomy was performed. This procedure has been performed by the laboratory of Dr. Mark Preul at the Barrow Neurological Institute, who will instruct on the model and provide input in surgical techniques. In both animals, a lateral hemisection of the left spinal cord was performed at T_9-10. MRI was done on a 3 T MRI scanner using a 5 cm wrist RF coil. For MRI, rats were anesthetized with ketamine, and the site of injury was localized by visualization of the vertebrae in a scout three-plane spoiled gradient echo pulse sequence. Gradient echo images were acquired at 0.2×0.2×1 mm resolution, and the spinal cord was easily identified in such images. Surgical microscopy of the injury site is also shown. Thus, MRI of the spinal cord after injury and reporter gel injections is feasible at 3 T, and will allow noninvasive detection of reporter gels after they are implanted.

REFERENCES

1. Lukashev M E W Z. ECM signalling: orchestrating cell behaviour and misbehaviour. *Trends Cell Biol.* 1998; 8(11):437-441.
2. Perris R P D. Role of the extracellular matrix during neural crest cell migration. *Mech Dev.* 2000; 95(1-2):3-21.
3. Assoian R K K E. Growth control by intracellular tension and extracellular stiffness. *Trends Cell Biol.* 2008; 18(7): 347-352.
4. Avraamides C J G-S B, Varner J A. Integrins in angiogenesis and lymphangiogenesis. Nat Rev Cancer. 2008; 8(8):604-617.
5. Schneiderbauer M M D C, Scully S P. Signalling "crosstalk" between TGF-beta1 and ECM signals in chondrocytic cells. *Cell Signal.* 2004; 16(10):1133-1140.
6. Stern R. Hyaluronidases in cancer biology. *Semin Cancer Biol.* 2008; 18(4):318-326.
7. Wang D A J, Gladson C L. The role of extracellular matrix in angiogensis in malignant glioma tumors. *Brain Pathol.* 2005; 15(4):318-326.
8. Bignami A A R. Some observations on the localization of hyaluronic acid in adult, newborn and embryonal rat brain. *Int J Dev Neurosci.* 1992; 10(1):45-57.
9. Bjorklund M K E. Gelatinase-mediated migration and invasion of cancer cells. *Biochim Biophys Acta.* 2005; 1775(1):37-69.
10. D'abaco G M K A. Integrins: molecular determinanats of glioma invasion. *J Clin Neurosci.* 2007; 14(11):1041-1048.
11. Daley W P P S, Larsen M. Extracellular matrix dynamics in development and regenerative medicine. *J Cell Sci.* 2008; 121 (pt 3).
12. D E I. Can cancer be reversed by engineering the tumor microenvironment? *Semin Cancer Biol.* 2008; 18(8):356-364.
13. SA M. Cell adhesion molecules: potential therapeutic & diagnostic implications. *Mol. Biotechnol.* 2008; 38(1):33-40.
14. Melrose J, Hayes A J, Whitelock J M, Little C B. Perlecan, the "jack of all trades" proteoglycan of cartilaginous weight-bearing connective tissues. *Bioessays.* 2008; 30(5):457-469.
15. Park Y L M, Hubbel J A, Hunziker E B, and Wong M. Bovine primary chondrocyte culture in synthetic matrix metalloproteinase-sensitve poly(ethylene glycol)-Based hydrogels as a scaffold for cartilage repair. *Tissue Engineering.* 2004; 10(3/4):515-522.
16. Novikov L N N L, Mosahebi A, Wiberg M, Terenghi G, Kellerth J O. A novel biodegradable implant for neuronal rescue and regeneration after spinal cord injury. *Biomaterials.* 2002; 23(16):3369-3376.
17. Li F, Griffith, M. Li Z. Tanodekaew, S. Sheardown, H, Hakim M. Carlsson D J. Recruitment of multiple cell lines by collagen-synthetic copolymer matrices in corneal regeneration. *Biomaterials.* 2005; 26(16):3093-3104.
18. Horn E M B M, Shu X Z, Harvey A, Prestwitch G D, Horn K M, Givson A R, Preul M C, Panitch A. Influence of cross-linked hyaluronic acid hydrogels on neurite outgrowth and recovery from spinal cord injury. *J Neurosurg Spine.* 2007; 6(2):133-140.
19. CS C. Towards a functional radiopaque hydrogel for nucleus pulposus replacement. *J Biomed Mater Res B Appl Biomater.* 2007; 83(2):440-450.
20. Jones L L S D, Tuszynski M H. Axonal regeneration through regions of chondroitin sulfate proteoglycan deposition after spinal cord injury: a balance of permissiveness and inhibition. *J. Neurosci.* 2003 23(28):9276-9288.
21. Kutschka I C I, Kofidis T, Arai T, von Degenfeld G, Sheikh A Y, Hendry S L, Pearl J, Hoyt G, Sista R, Yang P C, Blau H M, Gambhir S S, Robbins R C. Collagen matrices enhance survival of transplanted cardiomyoblasts and contribute to functional improvement of ischemic rat hearts. *Circulation,* 2006; 4(114):1167-173.
22. Lutolf M P L-F J, Schmoelkel H G, Metters A T, Weber F E, Fields G B, and Hubbel J A. Synthetic matrix metalloproteinase-sensitive hydrogels for the conduction of tissue regeneration: Engineering cell invasion characteristics. *Proc Nat Acad. Sci.* 2003; 100(9):5413-5418.
23. Piantino J B J, Boldberg D, Langer R, Benowitz L I. An injectable, biodegradable hydrogel for trophic factor delivery enhances axonal rewiring and improves performance after spinal cord injury. *Exp Neurol.* 2006; 201(2): 359-367.
24. Ramaswamy S W D, Fishbein K W, Elisseeff J H, Spencer R G. An analysis of the integration between articular cartilage and nondegradable hydrogel using magnetic resonance imaging. *J Biomed Mater Res B Appl Biomater.* 2006; 77(1):144-148
25. Schindler M N-E-K A, Ahmed I, Kamal J, Liu H Y, Amor N, Ponery A S, Crockett D P, Grafe T H, Chung H Y, Weik T, Jones E, and Meiners S. Living in three dimensions: 3D nanostructured environments for cell culture and regenerative medicine. *Cell Biochem Biophys.* 2006; 45(2): 215-227.
26. Tian W M Z C, Hou S P, Yu X, Cui F Z, Xu Q Y, Sheng S L, Cui H, Li H D. Hyaluronic acid hydrogel as Nogo-66 receptor antibody delivery system for the repairing of injured rat brain: in vitro. *J Control Release.* 2005; 102(1):13-22
27. Weissleder R P K, Wilkinson R, Zhou C, Bogdanov A Jr. Quantitation of slow drug release from an implantable and degradable gentamicin conjugate by in vivo magnetic resonance imaging. *Antimicrob Agents Chemother.* 1995; 39(4):839-845.
28. Zhanwu Cui B H L, Brent Vernon. New hydrolysis-dependent thermosensitive polymer for an injectable degradable system. *Biomacromolecules.* 2007; 8:1280-1286.

29. Luker G D L K. Optical imaging: current applications and future directions. *J Nucl Med.* 2008; 49(1):1-4.

30. Hammoud D A H J, Pomper M G. Molecular neuroimaging: from conventional to emerging techniques. *Radiology.* 2007; 245(1):21-42.

31. Arribas S M D C, Gonzalez M C, McGrath J C. Imaging the vascular wall using confocal microscopy. *J. Physiol.*; 584(Pt1):5-9.

32. Weissleder R P M. Imaging in the era of molecular oncology. *Nature.* 2008; 452(7187):580-589.

33. Tan J D P, Mclaren W J. Confocal endomicroscopy: a novel imaging technique for in vivo histology of cervical intraepithelial neoplasia. *Expert Rev Med. Devices.* 2007; 4(6):863-871.

34. E M H. Optical brain imaging in vivo: techniques and applications from animal to man. *J Biomed Opt.* 2007; 12(5):051402.

35. Querol M B A J. Environment-sensitive and enzyme-sensitive MR contrast agents. *Handb Exp Pharmacol.* 2008; 185 Pt 2:37-57.

36. Sherry A D W M. Chemical exchange saturation transfer contrast agents for magnetic resonance imaging. *Annu Rev Biomed Eng.* 2008; 10:391-411.

37. Petet M F G K, Jacobs M A, Pathak A P, Bhujwalla Z M. Molecular and functional MRI of the tumor microenvironment. *J Nucl Med.* 2008; 49(5):687-690.

38. A J. MRI contrast agents for functional molecular imaging of brain activity. *Curr Opin Neurobiol.* 2007; 17(5):593-600.

39. Gilad A A W P J, van ZijI PC, Bulte J W. Developing MR reporter genes: promises and pitfalls. *NMR Biomed.* 2007; 20(3):275-290.

40. Bull S R G M, Bras R E, Meade T J, Stupp S I. Self-assembled peptide amphiphile nanofibers conjugated to MRI contrast agents. *Nano Lett.* 2005; 5(1):1-4.

41. Bull S R G M, Bras R E, Venkatasubramanian P N, Stupp S I, Meade T J. Magnetic resonance imaging of self-assembled biomaterial scaffolds. *Bioconj Chem.* 2005; 16(6):1343-1348.

42. Czerski L M A, Ng T C, Vijayakumar S, Weichselbaum R. Growth and magnetic resonance characteristics of human squamus cell carcinoma xenografts implanted with cells suspended in Matrigel. *NMR Biomed.* 1993; 6(5):297-301.

43. Gordon M J C K, Margaritis A, Martin A J, Ethier C R, Rutt B K. Measurement of Gd-DTPA diffusion through PVA hydrogel using a novel magnetic resonance imaging method. *Biotechnol Bioeng.* 1999; 65(4):459-467

44. Gore J C B M, Zhong J, Mueller K F, Good W. NMR relaxation of water in hydrogel polymers: a model for tissue. *Magn Reson Med.* 1989; 9(3):325-332.

45. Ramaswamy S U M, Ieen S, Bajaj P, Fishbein K W, Spencer R G. Noninvasive assessment of glycosaminoglycan production in injectable tissue-engineered cartilage constructs using magnetic resonance imaging. *Tissue Eng Part C Methods.* 2008; 14(3):243-249.

46. Wunderbaldinger P J L, Weissleder R. Crosslinked iron oxides (CLIO): a new platform for the development of targeted MR contrast agents. *Acad Radiol.* 2002; 9(Suppl 2):S304-306.

47. Zhao M J L, Tang Y, Weissleder R. Magnetic sensors for protease assays. *Angew Chem Int Ed Engl.* 2003; 42(12): 1375-1378.

48. Laurent S F D, Port M, Roch A, Robic C, Vander Elst L, Muller R N. Magnetic iron oxide nanoparticles: synthesis, stabilization, vectorization, physicochemical characterizations, and biological applications. *Chem. Rev.* 2008; 108(6):2064-2110.

49. Hoehn M W D, Justicia C, Ramos-Cabrer P, Kruttwig K, Farr T, Himmelreich U. Cell tracking using magnetic resonance imaging. *J. Physiol.* 2007; 584(Pt 1):25-30.

50. Frank S L P. Voltage-sensitive magnetic gels as magnetic resonance monitoring agents. *Nature.* 1993; 363(6427): 334-336.

51. Hong R C M, Weissleder R, Josephson L. Magnetic microparticle aggregation for viscosity determination by MR. *Magn Reson Med.* 2008; 59(3):515-520.

52. Matsumoto Y J A. T2 relaxation induced by clusters of superparamagnetic nanoparticles: Monte Carlo simulations. *Magn Reson Imaging.* 2008; 26(7):994-998.

53. Bennett K M EMS, C. H. Sotak, and A. P. Koretsky. Controlled aggregation of ferritin to modulate MRI relaxivity. *Biphys J.* 2008 95(1):342-351.

54. Wood J C F J, Meade T. Mimicking liver iron overload using liposomal ferritin preparations. *Magn Reson Med.* 2004; 51(3):607-611.

55. Neurath H W K. Role of Proteolytic enzymes in biological regulation (A Review). *Proc Nat Acad. Sci.* 1976; 73(11):3825-3832.

56. Kaufmann S H L S, Meng X W, Loegering D A, Kottke T J, Henzing A J, Ruchaud S, Samejima K, Earnshaw W C. Apoptosis-associated caspase activation assays. *Methods.* 2008; 44(3):262-272.

57. Segers K D B, Nicolaes G A. Coagulation factor V and thrombophilia: background and mechanisms. *Thromb Haemost.* 2007; 98(3):530-542.

58. R A H J P W. Control of matrix metalloproteinase catalytic activity. *Matrix Biol.* 2007; 26(8):587-596.

59. Lerch M M H W, Kruger B. The role of cysteine proteases in intracellular pancreatic serine protease activation. *Adv Exp Med. Biol.* 2000; 477:403-411.

60. Wang S F C T, Zhang Z L, Shen X C, Lu Z X, Pang D W, Wong K Y. Direct electrochemistry and electrocatalysis of heme proteins entrapped in agarose hydrogel films in room-temperature ionic liquids. *Langmuir.* 2005; 21(20):9260-9266.

61. Bennett K M Z H, Sumner J P, Dodd S J, Bouraoud N, Doi K, Star R A, Koretsky A P. MRI of the basement membrane using charged nanoparticles as contrast agents. *Magn Reson Med.* 2008; 60(3):564-574.

62. Thompson C J, Chase G G, Yarin A L, Reneker D H. Effects of parameters on nanofiber diameter determined from electrospinning model. *Polymer.* 2007; 48:6913-6922.

63. Gupta P, Elkins C, Long T E, Wilkes G L. Electrospinning of linear homopolymers of poly(methyl methacrylate): exploring relationships between fiber formation, viscosity, molecular weight and concentration in a good solvent. *Polymer.* 2005; 46(13):4799-4810.

64. Zong X H, Kim K, Fang D F, Ran S F, Hsiao B S, Chu B. Structure and process relationship of electrospun bioabsorbable nanofiber membranes. *Polymer.* 2002; 43(16): 4403-4412.

65. Meldrum F C, B. R. Heywood, and S. Mann. Magnetoferritin: in vitro synthesis of a novel magnetic protein. *Science.* 1992; 257(5069):522-523.

66. Bulte J, Douglas T, Mann S, Frankel R B, Moskowitz B M, Brooks R A, Baumgarner C D, Vymazal J, Frank J A. Magnetoferritin. Biomineralization as a novel molecular approach in the design of ironoxide-based magnetic resonance contrast agents. *Invest Radiol.* 1994; 29(Suppl 2):S214-216.

67. Bulte J W, T. Douglas, S. Mann, R. B. Frankel, B. M. Moskowitz, R. A. Brooks, C. D. Baumgarner, J. Vymazal, M. P. Strub, and J. A. Frank. Magnetoferritin: characterization of a novel superparamagnetic MR contrast agent. *J Magn Reson Imaging.* 1994; 4(3):497-505.

68. Bulte J W D T, Mann S, Vymazal J, Iaughlin P G, Frank J A. Initial assessment of magnetoferritin biokinetics and proton relaxation enhancement in rats. *Acad Radiol.* 1995; 2(10):871-878.

69. Danon D, L. Goldstein, Y. Marikovsky, and E. Skutelsky. Use of cationized ferritin as a label of negative charges on cell surfaces. *J Ultrastruct Res.* 1972; 38(5):500-510.

70. Pilatus U A E, Artemov D, Mori N, Gillies R J, and Bhujwalla Z M. Imaging prostate cancer invasion with multi-nuclear magnetic resonance methods: The metabolic Boyden chamber. *Neoplasia.* 2000; 2(3):273-279.

71. Massia S P S J. Immobilized RGD peptides on surface-grafted dextran promote biospecific cell attachment. *Journal Of Biomedical Materials Research.* 2001; 56(3):390-399.

72. Massia S P S J, Letbetter D S. Surface-immobilized dextran limits cell adhesion and spreading. *Biomaterials.* 2000; 21(22):2253-2261.

73. Massia S P H M, Ehteshami G R. In vitro assessment of bioactive coatings for neural implant applications. *Journal Of Biomedical Materials Research Part A.* 2004; 68A(1):177-186.

74. Weng L P H, Chen W. Self-crosslinkable hydrogels composed of partially oxidized hyaluronan and gelatin: in vitro and in vivo responses. *J Biome Mater Res A.* 2008; 85(2):352-365.

The invention claimed is:

1. A method for non-invasively assessing molecular structure of a biodegradable hydrogel, the steps of the method comprising:
   a) functionalizing contrast agents to be used to monitor polymerization status of one or more macromolecules of the biodegradable hydrogel using magnetic resonance imaging (MRI);
   b) preparing the hydrogel from the macromolecules that are mixed with or attached to the contrast agents;
   c) subjecting the hydrogel to magnetic resonance (MR) analysis;
   d) monitoring degradation of the hydrogel based on changes in at least one of MR relaxation times T1 and T2, wherein the changes are due to presence of the contrast agents in the hydrogel; and
   e) monitoring aggregation of the contrast agents to report on the polymerization status of the macromolecules of the biodegradable hydrogel.

2. The method of claim 1, wherein said contrast agent comprises a metal ion selected from the group consisting of suitable Gd(III), Mn(II), Cu(II), Cr(III), Fe(III), Co(II), Er(II), Ni(II), Eu(III) and Dy(III).

3. The method of claim 1, wherein said contrast agent comprises a superparamagnetic iron oxide (SPIO).

4. The method of claim 1, wherein said contrast agent comprises a SPIO-containing nanoparticle.

5. The method of claim 1, wherein said contrast agent comprises ferritin bound to an iron oxide moiety.

6. The method of claim 1, wherein said hydrogel is made from a biocompatible, biodegradable polymer selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly (malic acid), poly(amino acids), poly(methyl vinyl ether), poly(maleic anhydride), chitin, chitosan, and copolymers, terpolymers, or higher poly-monomer polymers thereof or combinations or mixtures thereof.

7. The method of claim 1 wherein said hydrogel is made of a polymeric material that comprises one or more recurring units selected from linear (siloxanyl)alkyl (meth)acrylates, branched (siloxanyl)alkyl (meth)acrylates, cyclic (siloxanyl) alkyl (meth)acrylates, silicone-containing (meth)acrylates, fluorine-containing (meth)acrylates, hydroxyl group containing (meth)acrylates, (meth)acrylic acid, N-(meth)acryloylpyrrolidone, (meth)acrylamides, aminoalkyl (meth) acrylates, alkoxy group-containing (meth)acrylates, aromatic group containing (meth)acrylates, glycidyl (meth) acrylate, tetrahydrofurfuryl (meth)acrylate, silicone-containing styrene derivatives, fluorine-containing styrene derivatives, styrene derivatives, and vinyl monomers.

8. The method of claim 1, wherein said hydrogel is an extracellular matrix gel.

9. The method of claim 8, wherein said extracellular matrix gel is collagen or Matrigel®.

10. A method for non-invasively assessing molecular structure of a biodegradable hydrogel, the steps of the method comprising:
    a) functionalizing contrast agents to be used to monitor polymerization status of one or more macromolecules present in the biodegradable hydrogel using magnetic resonance imaging (MRI);
    b) preparing the hydrogel from the macromolecules that are mixed with or attached to the contrast agents;
    c) subjecting the hydrogel to magnetic resonance (MR) analysis; and
    d) monitoring degradation of the hydrogel based on changes in MR parameters, wherein the changes are due to presence of the contrast agents in the hydrogel, wherein said hydrogel further comprises a zymogen wherein said zymogen is activated in vivo initiate degradation of said hydrogel.

11. The method of claim 1 wherein said hydrogel comprises between 50 nM to 20 mM paramagnetic contrast agent.

12. The method of claim 10, wherein said hydrogel comprises between 1 µM and 1 mM zymogen.

13. The method of claim 10, wherein said zymogen is selected from the group consisting of a trypsinogen, a heparinase, a hyaluronidase, a chymotrypsinogen, a pepsinogen, a caspase, a proelastase, and a prolipase.

14. The method of claim 1, wherein the polymerization status is altered by cells.

15. The method of claim 1, wherein the polymerization status is altered by enzyme.

16. The method of claim 1, wherein the hydrogel further comprises cells.

17. The method of claim 10, wherein said contrast agent comprises a metal ion selected from the group consisting of suitable Gd(III), Mn(II), Cu(II), Cr(III), Fe(III), Co(II), Er(II), Ni(II), Eu(III) and Dy(III).

18. The method of claim 10, wherein said contrast agent comprises a superparamagnetic iron oxide (SPIO).

19. The method of claim 10, wherein said contrast agent comprises a SPIO-containing nanoparticle.

20. The method of claim 10, wherein said contrast agent comprises ferritin bound to an iron oxide moiety.

* * * * *